United States Patent
Caplice

(10) Patent No.: US 10,279,083 B2
(45) Date of Patent: May 7, 2019

(54) IGF-I FOR MYOCARDIAL REPAIR

(71) Applicant: UNIVERSITY COLLEGE CORK, NATIONAL UNIVERSITY OF IRELAND, CORK, Cork (IE)

(72) Inventor: Noel Caplice, Co. Cork (IE)

(73) Assignee: University College Cork, National University of Ireland, Cork, Cork (IE)

( * ) Notice: Subject to any disclaimer, the term of this patent is extended or adjusted under 35 U.S.C. 154(b) by 0 days.

(21) Appl. No.: 15/498,860

(22) Filed: Apr. 27, 2017

(65) Prior Publication Data

US 2017/0281830 A1 Oct. 5, 2017

Related U.S. Application Data

(63) Continuation of application No. 13/132,087, filed as application No. PCT/IE2009/000084 on Nov. 27, 2009, now Pat. No. 9,669,134.

(60) Provisional application No. 61/118,829, filed on Dec. 1, 2008.

(51) Int. Cl.
*A61F 2/06* (2013.01)
*A61L 29/04* (2006.01)
*A61L 29/16* (2006.01)

(52) U.S. Cl.
CPC ............. *A61L 29/048* (2013.01); *A61L 29/16* (2013.01); *A61L 2300/414* (2013.01); *A61L 2300/602* (2013.01)

(58) Field of Classification Search
CPC .... A61F 2/82; A61F 2250/0067; A61L 31/10; A61L 31/16; A61L 2300/416
See application file for complete search history.

(56) References Cited

U.S. PATENT DOCUMENTS

| | | | |
|---|---|---|---|
| 6,491,938 B2 * | 12/2002 | Kunz | A61K 9/0024 424/423 |
| 8,425,459 B2 | 4/2013 | Wang | |
| 2005/0125054 A1 * | 6/2005 | Bhat | A61L 27/54 623/1.42 |
| 2008/0255510 A1 * | 10/2008 | Wang | A61K 31/337 604/103.02 |

FOREIGN PATENT DOCUMENTS

| | | |
|---|---|---|
| WO | 2005/051229 | 6/2005 |
| WO | 2007/028053 | 3/2007 |

* cited by examiner

*Primary Examiner* — Christopher D. Prone
*Assistant Examiner* — Tiffany P Shipmon
(74) *Attorney, Agent, or Firm* — David S. Resnick; Nixon Peabody LLP

(57) ABSTRACT

Provided herein are methods for treating an individual having (suffering from) an acute myocardial infarction and drug eluting stents useful for treating such individuals. These methods include treating an individual by introducing, such as by surgically inserting, at a site of an acute coronary artery occlusion upstream of the site of acute myocardial infarction, a drug eluting stent (DES) that is capable of eluting from 25 pg to 950 pg of IGF-1 directly into the coronary circulation. The treatment is specifically directed to stimulation of repair or survival of damaged cardiac muscle or left ventricular remodeling.

7 Claims, 14 Drawing Sheets

Specification includes a Sequence Listing.

C

A

B

SEQUENCE LISTING

<160> NUMBER OF SEQ ID NOS: 17

<210> SEQ ID NO 1
<211> LENGTH: 20
<212> TYPE: DNA
<213> ORGANISM: Artificial
<220> FEATURE:
<223> OTHER INFORMATION: CD133 - forward primer

<400> SEQUENCE: 1
tcctggggtt gctgtttatt                                               20

<210> SEQ ID NO 2
<211> LENGTH: 21
<212> TYPE: DNA
<213> ORGANISM: Artificial
<220> FEATURE:
<223> OTHER INFORMATION: CD133 reverse primer

<400> SEQUENCE: 2
catatcacca agagggaaac g                                             21

<210> SEQ ID NO 3
<211> LENGTH: 18
<212> TYPE: DNA
<213> ORGANISM: Artificial
<220> FEATURE:
<223> OTHER INFORMATION: cKIT forward primer

<400> SEQUENCE: 3
gaggagataa atggaaac                                                 18

<210> SEQ ID NO 4
<211> LENGTH: 18
<212> TYPE: DNA
<213> ORGANISM: Artificial
<220> FEATURE:
<223> OTHER INFORMATION: cKIT human reverse primer

<400> SEQUENCE: 4
gaatcacgtt ttcttctc                                                 18

<210> SEQ ID NO 5
<211> LENGTH: 18
<212> TYPE: DNA
<213> ORGANISM: Artificial
<220> FEATURE:
<223> OTHER INFORMATION: cKIT pig reverse primer

<400> SEQUENCE: 5
gaatcacgtt tccgtctc                                                 18

<210> SEQ ID NO 6
<211> LENGTH: 25
<212> TYPE: DNA
<213> ORGANISM: Artificial
<220> FEATURE:
<223> OTHER INFORMATION: CD34 human forward primer

<400> SEQUENCE: 6
cctgatgaat cgccgcagct ggagc                                         25

<210> SEQ ID NO 7
<211> LENGTH: 25
<212> TYPE: DNA
<213> ORGANISM: Artificial

```
<220> FEATURE:
<223> OTHER INFORMATION: CD34 human reverse primer

<400> SEQUENCE: 7
ccagaaacgg ccattcagca agaca                                       25

<210> SEQ ID NO 8
<211> LENGTH: 25
<212> TYPE: DNA
<213> ORGANISM: Artificial
<220> FEATURE:
<223> OTHER INFORMATION: CD34 pig forward primer

<400> SEQUENCE: 8
gctgatgaac cgtcgcagtt ggagc                                       25

<210> SEQ ID NO 9
<211> LENGTH: 25
<212> TYPE: DNA
<213> ORGANISM: Artificial
<220> FEATURE:
<223> OTHER INFORMATION: CD34 pig reverse primer

<400> SEQUENCE: 9
ccagaaacgg ccattcagcg aggca                                       25

<210> SEQ ID NO 10
<211> LENGTH: 20
<212> TYPE: DNA
<213> ORGANISM: Artificial
<220> FEATURE:
<223> OTHER INFORMATION: Flk-1 forward primer

<400> SEQUENCE: 10
ttatcggaga agaacgtggt                                             20

<210> SEQ ID NO 11
<211> LENGTH: 20
<212> TYPE: DNA
<213> ORGANISM: Artificial
<220> FEATURE:
<223> OTHER INFORMATION: Flk-1 reverse primer

<400> SEQUENCE: 11
taatgctcag caggatggca                                             20

<210> SEQ ID NO 12
<211> LENGTH: 21
<212> TYPE: DNA
<213> ORGANISM: Artificial
<220> FEATURE:
<223> OTHER INFORMATION: eNOS forward primer

<400> SEQUENCE: 12
ggtatggatg agtatgacgt g                                           21

<210> SEQ ID NO 13
<211> LENGTH: 15
<212> TYPE: DNA
<213> ORGANISM: Artificial
<220> FEATURE:
<223> OTHER INFORMATION: eNOS reverse primer

<400> SEQUENCE: 13
tgttccggcc gaggg                                                  15
```

-continued

```
<210> SEQ ID NO 14
<211> LENGTH: 19
<212> TYPE: DNA
<213> ORGANISM: Artificial
<220> FEATURE:
<223> OTHER INFORMATION: VE-Cadherin forward primer

<400> SEQUENCE: 14
aacttcccct tcttcaccc                                                 19

<210> SEQ ID NO 15
<211> LENGTH: 17
<212> TYPE: DNA
<213> ORGANISM: Artificial
<220> FEATURE:
<223> OTHER INFORMATION: VE-Cadherin reverse primer

<400> SEQUENCE: 15
aaggctgctg gaaaatg                                                   17

<210> SEQ ID NO 16
<211> LENGTH: 24
<212> TYPE: DNA
<213> ORGANISM: Artificial
<220> FEATURE:
<223> OTHER INFORMATION: G3PDH forward primer

<400> SEQUENCE: 16
ccatgtcgtc atgggtgtga acca                                           24

<210> SEQ ID NO 17
<211> LENGTH: 25
<212> TYPE: DNA
<213> ORGANISM: Artificial
<220> FEATURE:
<223> OTHER INFORMATION: G3PDH reverse primer

<400> SEQUENCE: 17
gccagtagag gcagggatga tgttc                                          25
```

IGF-I FOR MYOCARDIAL REPAIR

CROSS REFERENCE TO RELATED APPLICATIONS

This application is a Continuation Application of currently pending U.S. Ser. No. 13/132,087, filed Jun. 13, 2011, which is a 371 National Phase Entry Application of International Application No. PCT/IE2009/000084 filed Nov. 27, 2009, which designates the U.S., and which claims benefit under 35 U.S.C. § 119(e) of U.S. Provisional Application No. 61/118,829 filed Dec. 1, 2008, the contents of which are incorporated herein by reference in their entirety.

SEQUENCE LISTING

The sequence listing of the present application has been submitted electronically via EFS-Web as an ASCII formatted sequence listing with a file name "Sequence-Listing-048262_070070_US", creation date of Apr. 26, 2017 and a size of 3,388 bytes. The sequence listing submitted via EFS-Web is part of the specification and is herein incorporated by reference in its entirety.

TECHNICAL FIELD

The invention relates to a stent suitable for implantation in the myocardial circulatory system and capable of delivering IGF-1 into the myocardial circulation. The invention also relates to a method of treating damaged cardiac muscle, especially cardiac muscle damaged by myocardial infarction, to stimulate survival and repair of damaged cardiac muscle, or stimulate left ventricular remodeling.

BACKGROUND TO THE INVENTION

Myocardial infarction (formation of an infarct or an area of dead heart muscle) occurs when the blood supply to the heart is interrupted, which can be the result of occlusion (blockage) of a coronary artery, such as follows the rupture of vulnerable atherosclerotic plaque. Acute myocardial infarction (AMI) occurs as the result of sudden blockage of blood supply to the heart. Irreversible death of heart of heart muscle begins to occur if the blood supply is not re-established quickly enough (e.g., within 20 to 40 minutes).

If impaired blood flow to the heart lasts long enough, heart cells die, via necrotic and/or apoptotic cellular pathways, do not grow back and a collagen scar forms in their place. This can result in permanent damage to the heart and scar tissue also puts the patient at risk for potentially life threatening arrhythmias, and/or may result in the formation of a ventricular aneurysm.

Diseases of the heart, such as MI, are the leading cause of death for both men and women. Coronary heart disease is responsible for 1 in 5 deaths in the U.S. About 1.2 million people in the U.S. suffer anew or recurrent coronary attack every year and of them, approximately 400,000 of them die as a result of the attack.

STATEMENTS OF INVENTION

In one embodiment, the invention relates to a drug eluting stent suitable for intracoronary implantation, the stent comprising a stent body, and a coating covering at least a part of the stent body, wherein the coating comprises IGF-1 and is capable of releasing a therapeutic dose of from 25 pg to 950 pg IGF-1 into the coronary circulation over an elution period of up to 14 days.

The invention also relates to a stent having an IGF-1 eluting coating, wherein the coating is adapted to release a therapeutic dose of from 25 to 950 pg IGF-1 into the coronary circulation over an elution period of up to 14 days.

The invention further relates to a stent, typically suitable for intracoronary implantation, and having an IGF-1 eluting coating, the coating being loaded with a therapeutic dose of less than 1000 pg of IGF-1, wherein the coating is typically capable of eluting at least 50% of the IGF-1 loading over an elution period of suitably up to 14 days.

Suitably, the therapeutic dose of IGF-1 is from 250 pg to 750 pg, preferably 300 pg to 700 pg, preferably 350 pg to 650 pg, more preferably from 400 to 600 pg, more preferably from 400 to 550 pg, more preferably from 400 to 500 pg, more preferably from 420 to 480 pg. Typically, the therapeutic dose is at least 300 pg, 350 pg, 380 pg, 390 pg, 400 pg, 410 pg, 420 pg, 430 pg, or 440 pg IGF-1. Generally, the therapeutic dose is at most 700 pg, 650 pg, 600 pg, 550 pg, 500 pg, 490 pg, 480 pg, 470 pg, or 460 pg IGF-1.

In one embodiment, the coating is adapted for delivery of the therapeutic dose of IGF-1 into the coronary circulation over a period (the elution period) of between 1 hour and 14 days, preferably between 6 hours and 14 days, preferably between 12 hours and 14 days, preferably between 18 hours and 14 days, and preferably between 14 hours and 14 days. Generally, the coating is adapted for delivery of the therapeutic dose of IGF-1 over a period of from 12 hours to 14 days, preferably from 12 hours to 10 days, preferably from 12 hours to 9 days, preferably from 12 hours to 8 days, and preferably from 12 hours to 7 days. Generally, the coating is adapted for delivery of the therapeutic dose of IGF-1 over a period of from 20 hours to 9 days, preferably from 22 hours to 8 days, preferably from 24 hours to 7 days, preferably from 36 hours to 6 days, and preferably from 48 hours to 5 days.

In a preferred embodiment of the invention, the coating is adapted to deliver a therapeutic so dose of from 400 to 500 pg of IGF-1 into the myocardial circulation over a period of 12 hours to 7 days.

The term "elution period" preferably means the period for eluting the therapeutic dose of IGF-1 into the coronary circulation. Generally, the coating does not elute any further IGF-1 once the therapeutic dose has been eluted.

In one embodiment of the invention, the coating is loaded with less than 1000 pg, 900 pg, 800 pg, 700 pg, 650 pg, 600 pg, 550 pg, or 500 pg of IGF-1. Suitably, the stent is loaded with from 300 to 900 pg, preferably 350 to 850 pg, preferably 400 to 800 pg, preferably 450 to 750 pg, preferably 500 to 700 pg, of IGF-1.

In one preferred embodiment, the coating on the stent is prepared using PEP™ technology. The details of such coating technologies, and coatings prepared using the technology, are described in US Patent Application US2004/0241325 (Al-Lamee et al.) and generally involve priming the stent surface with a surface functional group, and then coating the functionalised surface with a mixture of drug and polymer adapted to react with the functionalised surface. The entire contents of US2004/024 1325 are incorporated herein by reference. In particular, the Examples 1 to 15 on pages 3 to 10 are incorporated herein by reference.

In one embodiment, the stents of the invention are adapted to deliver IGF-1 and a further cardioprotective agent into the myocardial circulation. Examples of such further cardioprotective agents are provided below.

In another aspect, the invention relates to a method of stimulating survival or repair of cardiac muscle or left ventricular remodeling, in a mammal having damaged cardiac muscle, comprising the step of implanting a stent of the invention into a coronary artery of the mammal upstream of the site of the damaged cardiac muscle. Typically, the mammal being treated has suffered a myocardial infarction, for example an acute MI, although the method of treatment may be in response to damaged cardiac muscle caused by other events, for example, ischemia or trauma.

The invention also provides a method of treating a mammal that has suffered a myocardial infarction to stimulate repair or survival of cardiac muscle damaged by the infarct, or to stimulate left ventricular remodeling, the method comprising a step of implanting a stent of the invention into a coronary artery of the mammal upstream of the site of the damaged cardiac muscle.

The invention also relates to a method of stimulating survival or repair of cardiac muscle, or stimulating left ventricular remodeling, in a mammal having damaged cardiac muscle, comprising the step of administering a therapeutic dose of IGF-1 to the damaged cardiac muscle by intracoronary delivery. Typically, the mammal being treated has suffered a myocardial infarction, although the method of treatment may be in response to damaged cardiac muscle caused by other events, for example ischemia or trauma. Suitably, the IGF-1 is administered by intracoronary infusion into the coronary circulation, although other methods of intracoronary delivery are envisaged such as for example intracoronary delivery by means of an IGF-1 eluting implantable device such as a stent. Typically, a therapeutic dose of between 25 pg and 950 pg IGF-1 is administered by intracoronary delivery, ideally over a period of from 1 second to 24 hours.

The invention also provides a method of treating a mammal that has suffered a myocardial infarction to stimulate repair or survival of cardiac muscle damaged by the infarct, or to stimulate left ventricular remodeling, the method comprising a step of administering a therapeutic dose of IGF-1 to the damaged cardiac muscle by intracoronary delivery. Typically, the mammal being treated has suffered a myocardial infarction, although the method of treatment may be in response to damaged cardiac muscle caused by other events, for example ischemia or trauma. Suitably, the IGF-1 is administered by intracoronary infusion into the coronary circulation, although other methods of intracoronary delivery are envisaged such as for example intracoronary delivery by means of an IGF-1 eluting implantable device such as a stent. Typically, a therapeutic dose of between 25 pg and 950 pg IGF-1 is administered by intracoronary delivery, ideally over a period of from 1 second to 24 hours.

In the methods of the invention, the therapeutic dose of IGF-1 is suitably from 50 to 900 pg, 100 to 850 pg, 150 to 800 pg, 200 to 750 pg, 300 pg to 700 pg, 350 pg to 650 pg, more preferably from 400 to 600 pg, more preferably from 400 to 550 pg, more preferably from 400 to 500 pg, more preferably from 420 to 480 pg. Typically, the therapeutic dose is at least 30 pg, 50 pg, 75 pg, 100 pg, 125 pg, 150 pg, 175 pg, 200 pg, 250 pg, 300 pg, 350 pg, 380 pg, 390 pg, 400 pg, 410 pg, 420 pg, 430 pg, or 440 pg IGF-1. Generally, the therapeutic dose is at most 900 pg, 850 pg, 800 pg, 750 pg, 700 pg, 650 pg, 600 pg, 550 pg, 500 pg, 490 pg, 480 pg, 470 pg, or 460 pg IGF-1.

In one embodiment, the coating is adapted for delivery of the therapeutic dose of IGF-1 into the coronary circulation over a period (the elution period) of between 1 hour and 14 days, preferably between 6 hours and 14 days, preferably between 12 hours and 14 days, preferably between 18 hours and 14 days, and preferably between 14 hours and 14 days. Generally, the coating (or stent) is adapted for delivery of the therapeutic dose of IGF-1 over a period of from 12 hours to 14 days, preferably from 12 hours to 10 days, preferably from 12 hours to 9 days, preferably from 12 hours to 8 days, and preferably from 12 hours to 7 days. Generally, the coating is adapted for delivery of the therapeutic dose of IGF-1 over a period of from 20 hours to 9 days, preferably from 22 hours to 8 days, preferably from 24 hours to 7 days, preferably from 36 hours to 6 days, and preferably from 48 hours to 5 days.

Suitably, the therapeutic dose is administered in a plurality of doses, for example between 1 and 100 individual doses. Ideally, the IGF-1 is delivered by intracoronary infusion. Preferably, the IGF-1 is administered within 1 hour, 2 hours, 3 hours, 4 hours, 5 hours, 6 hours, 8 hours, 10 hours, 12 hours, 18 hours, 24 hours, 48 hours, 72 hours, of the cause of the damage (i.e. within 72 hours of the myocardial infarction event). Ideally, the therapeutic dose of IGF-1 is administered (i.e. infused) over a period of from 5 seconds to 1 hour, more preferably from 1 to 30 minutes, and even more preferably from 1 to 10 minutes. The period of infusion may involve a gradual infusion of the therapeutic dose of IGF-1, or a plurality of infusions interspersed with periods during which the IGF-1 is not infused (to allow the infused IGF-1 interact with the damaged cells). Thus, for example, the total infusion of three minutes may comprise three separate infusions of 30 seconds each, separated by 30 second non-infusion periods. In one embodiment, the IGF-1 is delivered through an angioplasty balloon. Suitably, the balloon is inflated for the periods of infusion, and typically deflated during the non-infusion periods. It will be clear that the therapeutic dose of IGF-1 is between and 950 pg which is required to be delivered to the damaged tissue over a period of time. Thus, a higher concentration of IGF-1 may be delivered over a shorter period of time, or a lower concentration of IGF-1 may be delivered over a longer period of time. For example, for intracoronary infusion of 450 pg of IGF-1, this may be delivered by three 30 second infusions of 5 ml of IGF-1 at a concentration of 30 pg/ml.

A: CPCs isolated from peripheral blood mononuclear cells were characterized for expression of progenitor markers using RT-PCR B: The CM from CPC was screened for presence of about 78 different cytokines of which the TGFβ2 and IFG1 were the predominant growth factors.

C: Conditioned media significantly protected the rat neonatal cardiomyocytes from apoptosis induced cell death, while blocking TGFβ and IGF1 using specific neutralizing antibodies abrogated the protective effects of conditioned media. For neutralizing of TGFβ and IGF1, the CM was incubated with TGFβ and/or IGF1 antibody for 15 minutes at 37° C. before exposing it to the cardiomyocytes.

D: Purified TGFβ and IGF1 peptides mimicked the effects of CM at a vary narrow dose range. The data is expressed as Mean±SEM of % Caspase 9 activity to that of X-Vivo group in three independently performed experiments.

Figure 2:
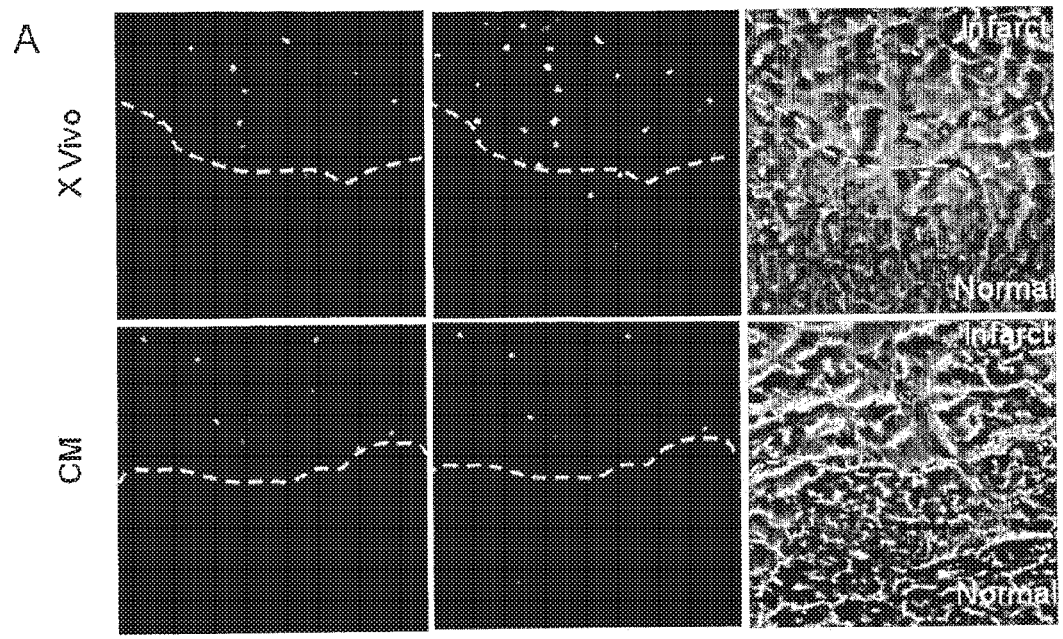
Figure 2:
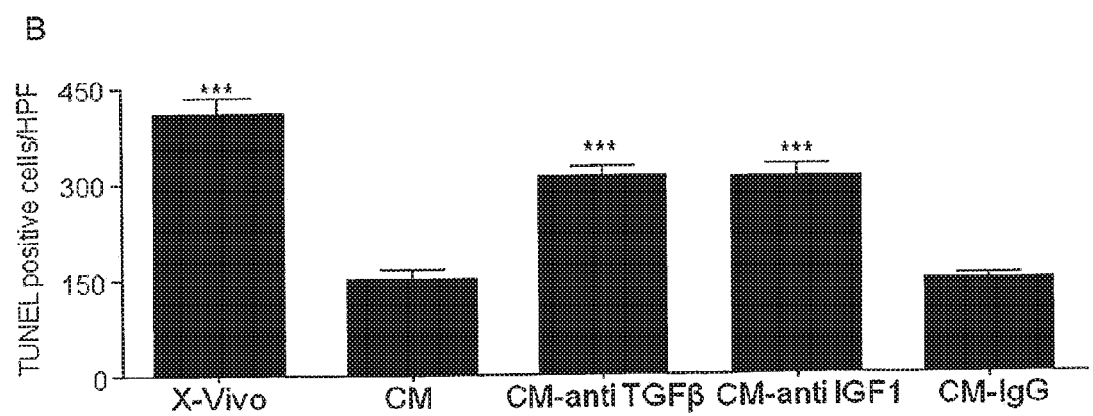
Figure 2:
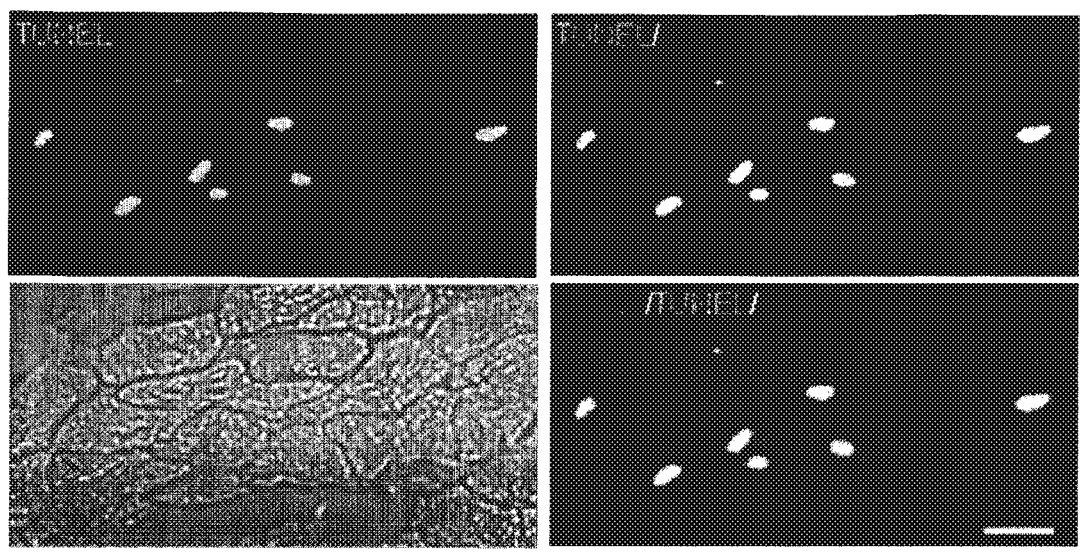

FIG. 2. TUNEL staining in borderzone myocardium (200×).

A: Conditioned media (CM) treated group had significantly (p<0.001) reduced TUNEL signals at the borderzone myocardium compared to the X-Vivo treated group.

B: The effects of CM were blocked by neutralizing TGFβ and IGF1 in CM. The TUNEL signals from 5 sections/pig (N=3-4) with an average of 5 High power fields/section is expressed as Mean±SEM C: A representative magnified (600×) image of border zone myocardium confirming the localization of TUNEL signal in the cardiomyocytes.

Figure 3:
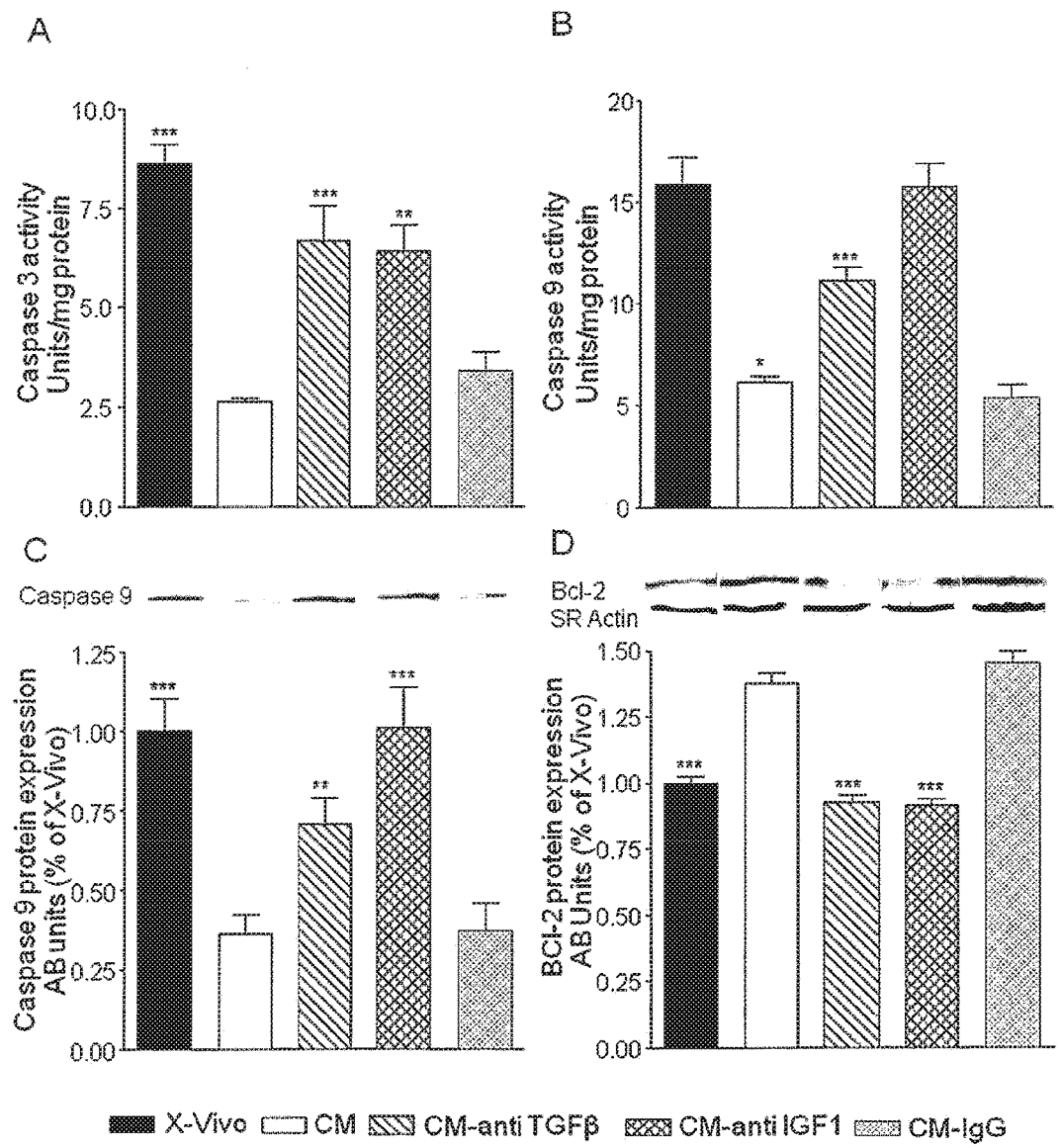

FIG. 3. Apoptotic signal in border zone myocardium 24 hrs post myocardial infraction. Caspase 3 activity (A), Caspase 9 activity (B), and Caspase 9 protein expression (C) were significantly (p0.0001) reduced in the conditioned media treated group while the anti-apoptotic protein BCL2 (D) was significantly upregulated. The anti-apoptotic effects of CM are mediated by TGFβ (p0.001) and IGF1 (p<0.01). The data are expressed as Mean±SEM of border zone myocardium samples from 3-4 pigs/group.

Figure 4:
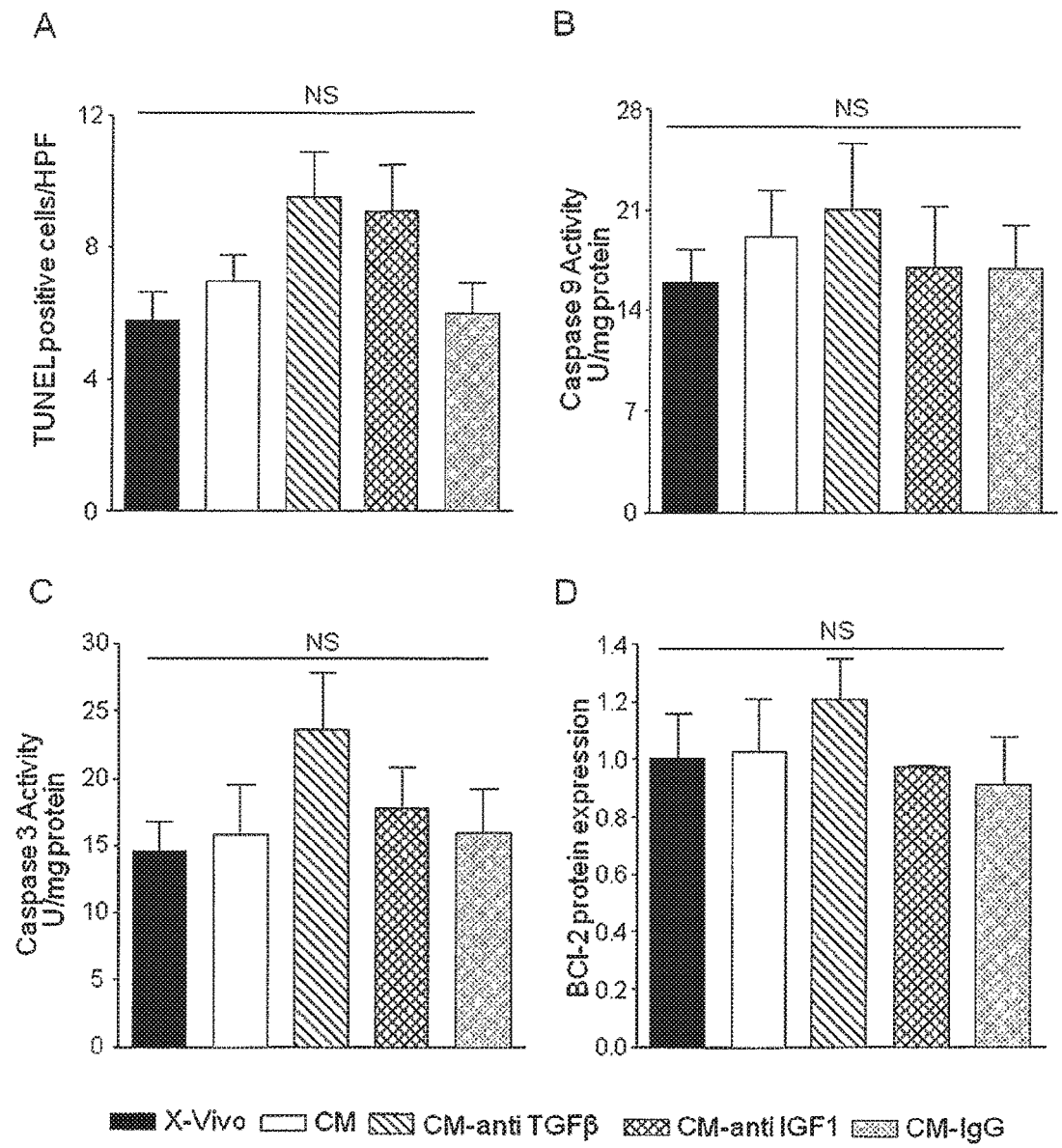

FIG. 4. Apoptotic signal in border zone myocardium 8 weeks post myocardial infraction. The apoptotic markers i.e., TUNEL positive nuclei (A), Caspase 9 activity (B). Caspase 3 activity (C) and BCL2 protein expression (D) were not effected at chronic time point (8 wks) post conditioned media therapy. The data are expressed as Mean±SEM of border zone myocardium samples from 3-4 pigs/group.

Figure 5:
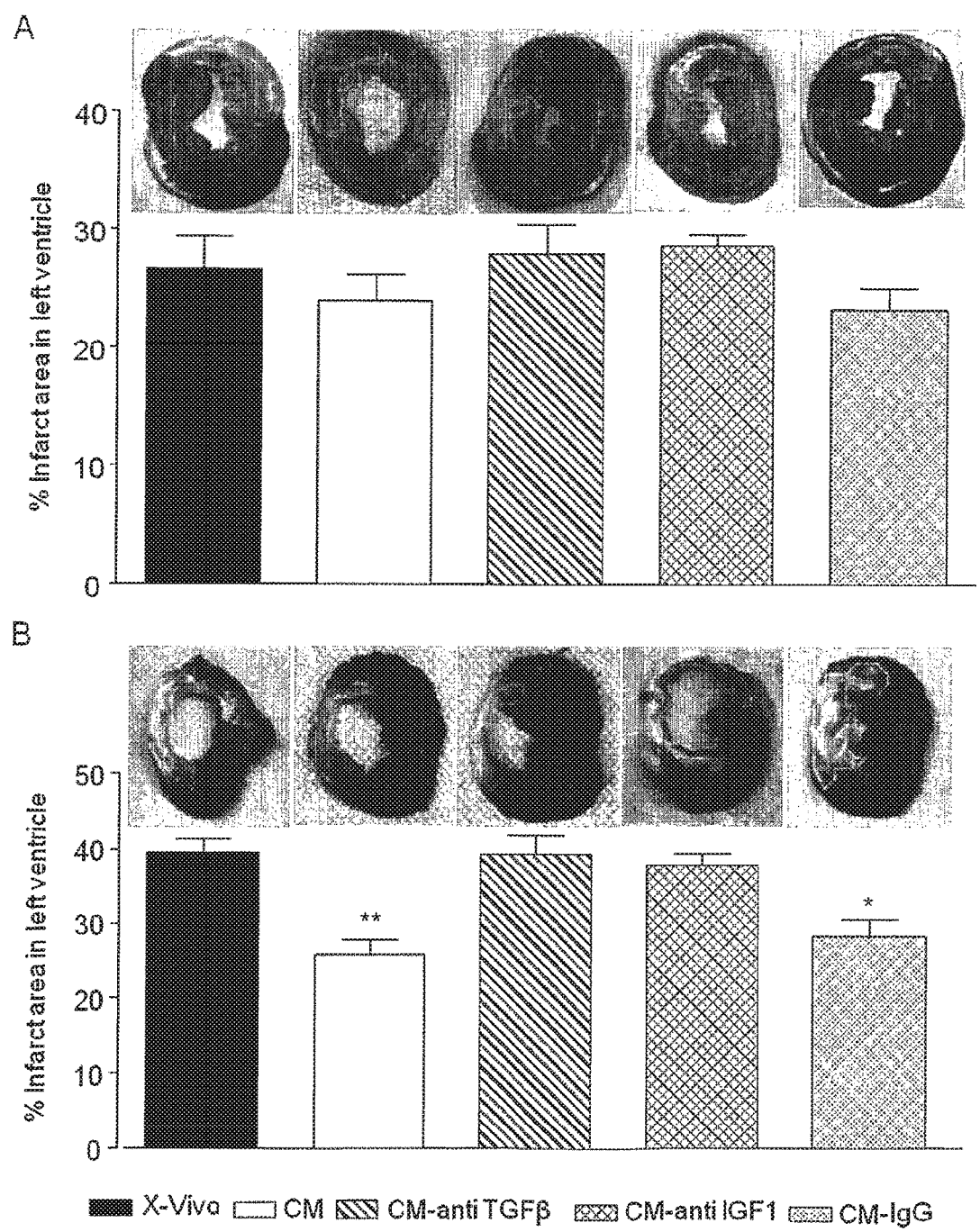

FIG. 5. Effect of conditioned media on left ventricular infarct area.

A: Conditioned media (CM) therapy did not influence the left ventricular infarct area at 24 hrs post MI.

B: However. CM therapy resulted in significant (P<0.01) reduction in the left ventricular infarct area at 8 weeks post MI. The data are expressed as Mean±SEM of 6-7 ventricular cross sections/pig heart with 3-4 pigs/group.

Figure 6:
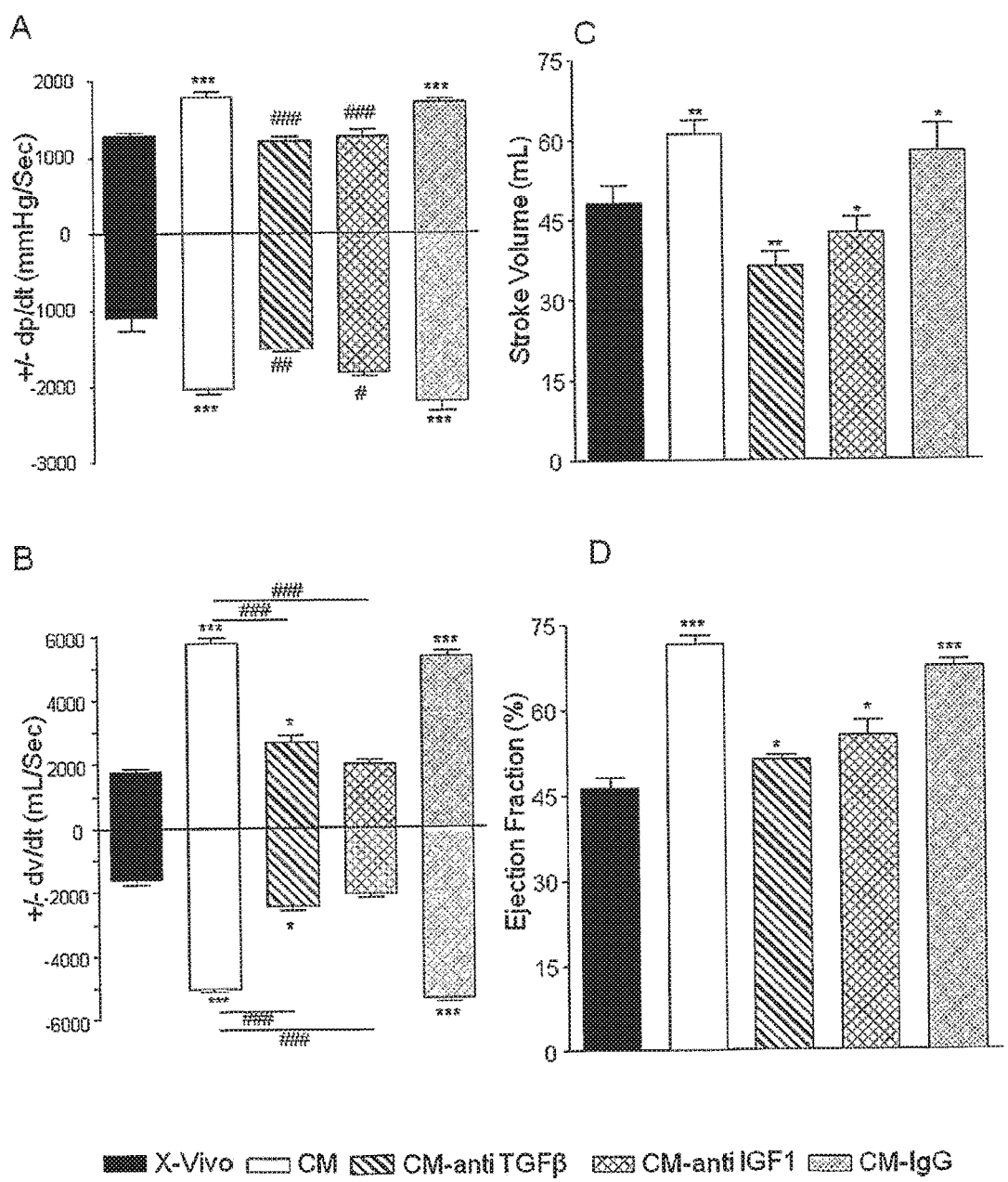

FIG. 6. Left ventricular functional analysis at 24 hrs post MI.

Conditioned media (CM) therapy significantly improved the left ventricular function i.e., ±dp/dt (A), ±dv/dt (B), stroke volume (C), and Ejection fraction (D) at 24 hrs post MI. The effects of CM appear to be mediated by TGF and IGF1. The data are expressed as Mean±SEM 20-25 cardiac cycles/pig with 3-4 pigs/group.

Figure 7:
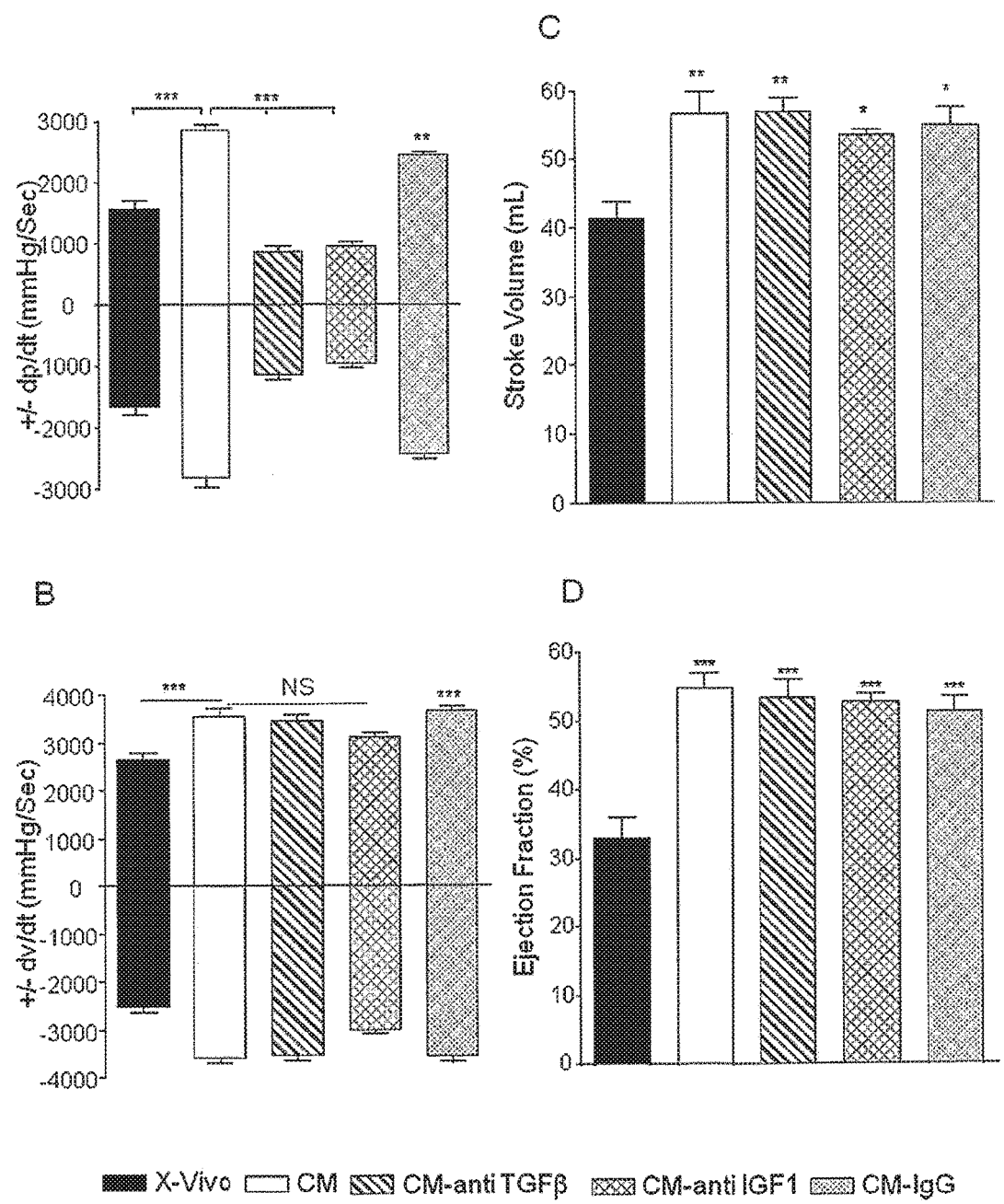

FIG. 7. Left ventricular functional analysis at 8 weeks post MI.

Conditioned media (CM) therapy significantly improved the left ventricular function i.e., ±dp/dt (A) ±dv/dt (B), stroke volume (C), and Ejection fraction (D) at 8 weeks post MI. The data are expressed as Mean±SEM 20-25 cardiac cycles/pig with 3-4 pigs/group.

Figure 8:
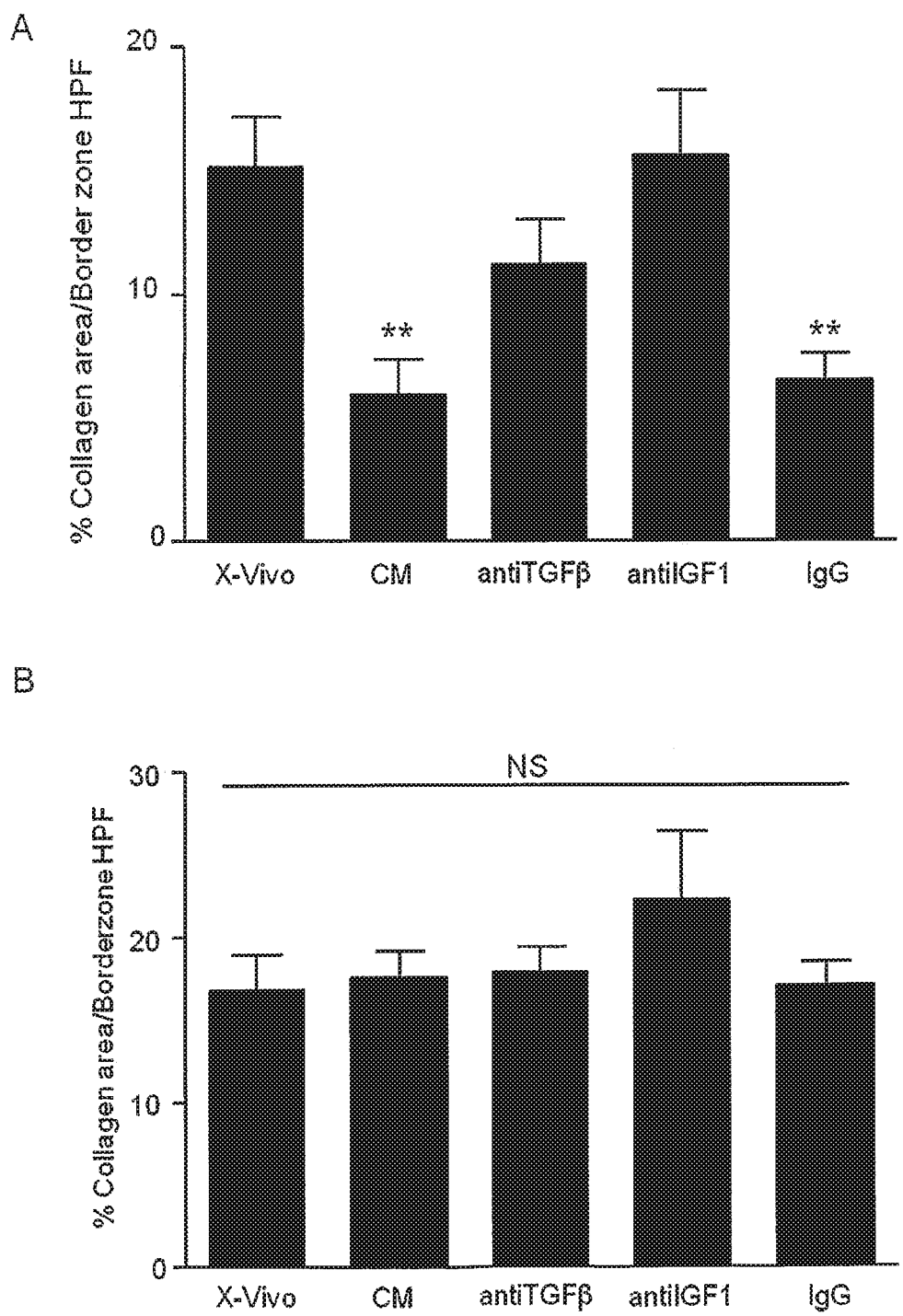

FIG. 8. Effect of Conditioned media (CM) on border zone collagen content at 24 hrs (A) and 8 weeks (B) post MI.

CM therapy significantly reduced the collagen content in the border zone myocardium at the acute (A) but not chronic (B) time frame. The border zone sections were stained for collagen using picrosirus red and quantified using the NIH imageJ software. Collagen staining with picrosirus red on 5 sections/pig (n=3-4) with an average of 5 High power fields/section is so expressed as Mean±SEM.

Figure 9:
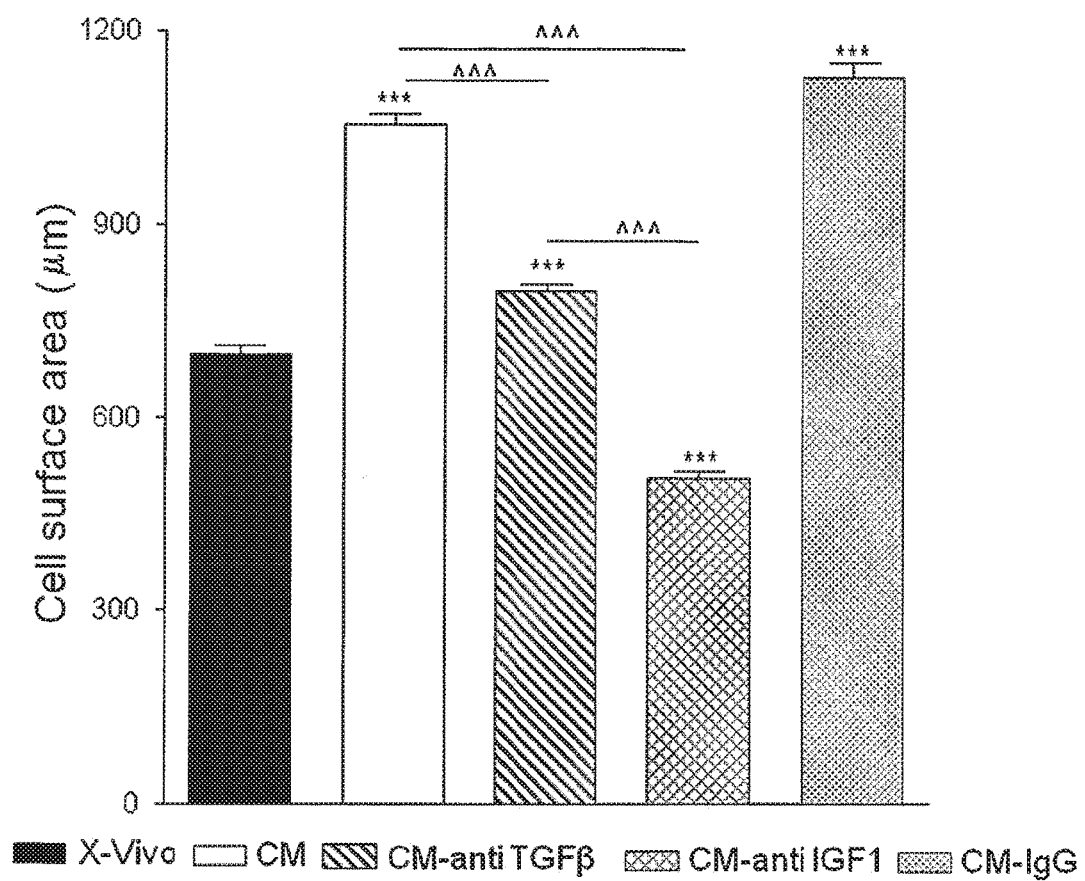

FIG. 9. Effects of Conditioned media (CM) on borderzone cardiomyocyte hypertrophy. CM significantly (p0.001) increased border zone cardiomyocyte hypertrophy at 8 weeks post myocardial infarction and this effect was mediated by TGF and IGF1. High power (600×) images of border zone cardiomyocyte were acquired using a NIKON confocal microscope and plainmetric analysis was performed using NIKON image analysis software to quantify cardiomyocyte size. An average of 300-400 border zone cardiomyocytes were analyzed per pig (with 3-4 pigs/group) and the data are reported as Mean±SEM of 1000-1600 cardiomyocytes/group.

Figure 10:
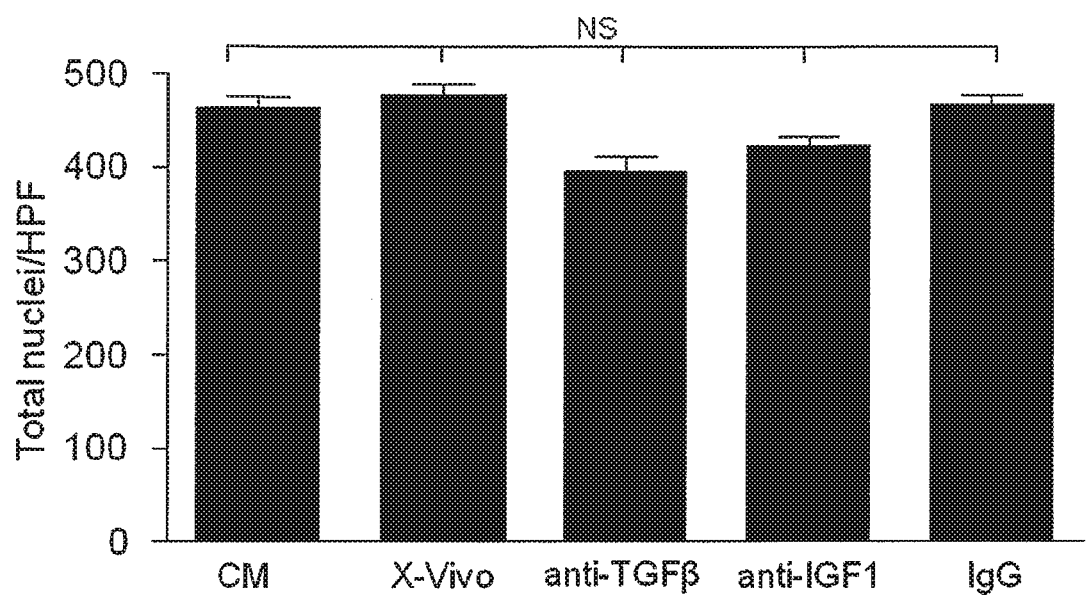

FIG. 10. Conditioned media therapy did not affect the total number of nuclei in the border zone myocardium. Total number of DAPI positive nuclei/High power field were counted and expressed as Mean±SEM of 10 sections/animal.

Figure 11:
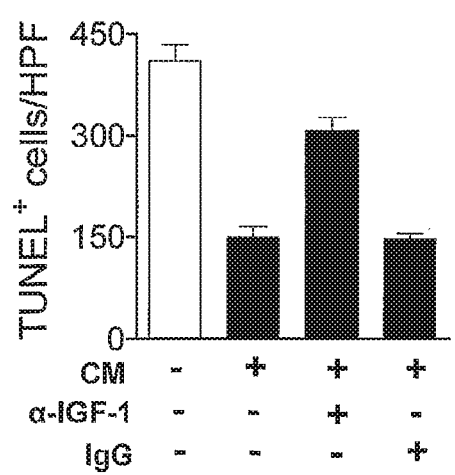

FIG. 11 Antiapoptotic effect of conditioned media (CM) therapy on borderzone (BZ) myocardium in vivo (TUNEL staining) was abrogated by blocking IGF-1 in CM using selective neutralizing antibody.

Figure 12:
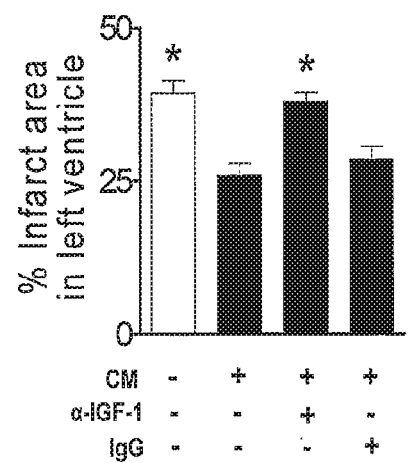
Figure 12:
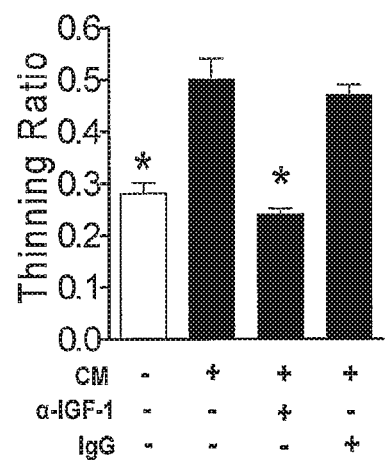

FIG. 12. Effect of conditioned media on left ventricular infarct area at 8 weeks (A) post myocardial infarction (MI) was significantly reduced by CM therapy, which also increased thinning ratio (B) at 8 weeks post MI.

Figure 13:
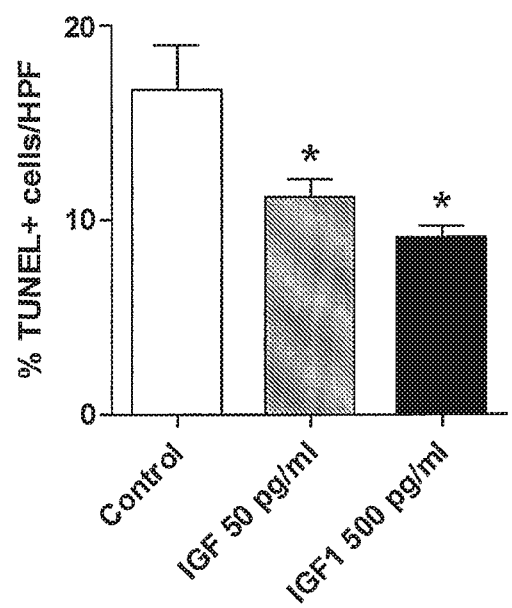

FIG. 13. Antiapoptotic effect of IGF1 (50 and 500 pg/ml) therapy on borderzone (BZ) myocardium in vivo.

DETAILED DESCRIPTION OF THE INVENTION

The application is based at least in part on the surprising finding that cytokines, such as two cytokines that are cellular factors secreted from endothelial progenitor cells (EPC). TGFβ1 (TGFBeta1) and IGF1, play a major role in cardiac repair after myocardial infarction (one result of which is formation of a myocardial infarct), such as acute myocardial infarction. These factors act as cardioprotective agents in that they exert anti-apoptotic and/or cardiotrophic and other beneficial effects on affected or diseased tissue, for example at the site of an acute myocardial infarction. Such cytokines exert their effects, for example, by reducing or preventing apoptosis in affected or diseased tissue and/or enhancing or facilitating regional border zone hypertrophy in healthy tissues and/or enhancing or facilitating angiogenesis in the border zone.

Provided herein are methods of treating an individual suffering from an acute myocardial infarction, comprising administering to the individual, upstream of the myocardial infarction, a therapeutically effective amount of a (at least one, one or more) cardioprotective agent. In specific embodiments, TGFβ1, IGF1, or TGFβ1 and IGF1 are administered to the individual, upstream of the myocardial infarction, in sufficient quantity to result in delivery to the heart of TGFβ1, IGF1 or TGFβ1 and IGF1 in concentrations that reduce effects of the myocardial infarction on the individual (e.g., by exerting anti-apoptotic and/or cardiotrophic and other beneficial effects on affected or diseased tissue, in particular by stimulating repair or survival of cardiac muscle or stimulating left ventricular remodeling).

In one embodiment, a therapeutically effective amount of a (at least one, one or more) cardioprotective agent is administered to the individual by means of a stent that comprises the cardioprotective agent and is suitably introduced at the site of an occlusion, upstream of the site of a myocardial infarction, such as upstream of the site of acute myocardial infarction. Typically, the stent is introduced across the occlusion. The cardioprotective agent is released from the stent in sufficient quantity and at an appropriate rate to result in delivery of the cardioprotective agent to the heart in an amount or concentration sufficient to assist or enhance repair of heart tissue and reduce (completely or partially) apoptosis of cardiomyocytes and, thus, reduce adverse effects on the heart. In specific embodiments in which a (at least one, one or more) cardioprotective agent is administered by means of a stent suitably inserted at the site of an occlusion, upstream of the site of acute myocardial infarction, the stent comprises (e.g., is coated or covered with, otherwise contains) an eluting factor that comprises the cardioprotective agent(s). The cardioprotective agent(s) are released from the eluting factor into the myocardial circulation and delivered to the heart via the circulation. In some embodiments, the cardioprotective agent(s) target the acute myocardial infarction border zone, which is a region of the heart (ventricle) between/that separates an area of grossly normal heart tissue and infarcted heart tissue. The infarct border zone is a site of moderately injured, partially perfused, potentially salvageable tissue, comprising myocytes, at the periphery of developing myocardial infarcts.

A stent is typically introduced, using methods known to those of skill in the art, into an individual at the time of an acute myocardial infarction (at the time or soon after he/she has a myocardial infarction), such as immediately, or within a few minutes to a few hours, or within up to 72 hours after the acute infarction occurs. For example, the stent is introduced within 5 minutes, 10 minutes, 15 minutes, 30 minutes, 45 minutes, 1 hour, 2 hours, 3 hours, 6 hours, 12 hours, 18 hours, 24 hours, 30 hours, 36 hours, 48 hours, or 72 hours after acute myocardial infarction. The cardioprotective agent(s) on a stent introduced into an individual is/are released from the stent within 5 minutes, 10 minutes, 15 minutes, 30 minutes, 45 minutes, 1 hour, 2 hours, 3 hours, 6 hours, 12 hours, 18 hours, 24 hours, 30 hours, 36 hours, 48 hours, or 72 hours after the stent is introduced into an individual. Release of the cardioprotective agent(s) begins soon after the stent is introduced and typically within an hour after stent introduction.

The cardioprotective agent(s) are released from the stent into the myocardial circulation at a concentration of about 0.01, about 0.1, about 1, about 10, about 100, or about 1000 pg/ml or any concentration in between. In the case of IGF-1, a therapeutic dose of from 250 to 750 pg is delivered into the myocardial circulation over a suitable period of time, generally up to 14 days.

In the methods described herein, TGFβ1, IGF1, or TGFβ1 and IGF1 can be administered in combination with other cardioprotective agents, such as other (different) cytokines, anti-coagulating agents, a vessel spasticity minimizing agents, a vasodilator agent, a calcium blocker agent, a sodium channel blocker agents, or an anti-inflammatory agents.

In another embodiment of the method of treating an individual suffering from an acute myocardial infarction, a therapeutically effective amount of a (at least one, one or more) cardioprotective agent is administered intravenously to the individual, upstream of the myocardial infarct. In specific embodiments, TGFβ1, IGF1, or TGFβ1 and IGF1 are administered intravenously to the individual in sufficient quantity to result in delivery of the cardioprotective agent to the heart in an amount or concentration sufficient to assist or enhance repair of heart tissue and reduce (completely or partially) apoptosis of cardiomyocytes and, thus, in particular, stimulate survival or repair of damaged cardiac muscle or stimulate left ventricular remodeling. In this embodiment, a cardioprotective agent(s) is administered intravenously at the time of myocardial infarction (immediately) or within a few minutes to a few hours, or within up to 72 hours after it has occurred. The dose of TGFβ1, IGF1, or TGFβ1 and IGF1 administered in this embodiment is approximately up to 5-fold higher, or 10-fold higher, or 50-fold higher, or 100-fold higher, or 500-fold higher, or up to 1000-fold higher than the dose administered into a coronary artery (e.g., than the dose administered via stent introduced into a coronary artery). In this embodiment as well, TGFβ1, IGF1, or TGFβ1 and IGF1 can be administered in combination with additional cardioprotective agents, such as other (different) cytokines, anti-coagulating agent, a vessel spasticity minimizing agent, a vasodilator agent, a calcium blocker agent, a sodium channel blocker agent, or an anti-inflammatory agent.

In addition, provided herein are drug eluting stents that can be introduced at the site of an acute coronary artery occlusion upstream of the site of acute myocardial infarction in order to treat an individual suffering from acute myocardial infarction. The drug eluting stents provided deliver a (at least one, one) cardioprotective factor, such as TGFβ1, IGF1, or TGFβ1 and IGF1, when present in (after being introduced into) the individual at the site and at the time of myocardial infarction or shortly thereafter (e.g., within 5 minutes, 10 minutes, 15 minutes, 30 minutes, 45 minutes, 1 hour, 2 hours, 3 hours, 6 hours, 12 hours, 18 hours, 24 hours, 30 hours, 36 hours, 48 hours, or 72 hours). The drug eluting stent of the invention not only serves to maintain vessel patency after angioplasty, but also acts as a regional drug delivery platform to enhance repair and reduce (partially or completely) apoptosis in the myocardium, such as in the infarct border zone.

The drug eluting stent of the invention, when surgically inserted, for example, at the site of an acute coronary artery occlusions upstream of the site of acute myocardial infarction, releases cardioprotective agent(s) that exert certain effects, such as anti-apoptotic and/or cardiotrophic effects, that are beneficial to an individual suffering from an acute myocardial infarction. The beneficial effects exerted by the cardioprotective agents of the invention, when provided sufficiently soon after the occurrence of myocardial infarction include a reduction or prevention of necrosis or apoptosis of myocytes, such as at the periphery of developing myocardial infarcts and/or an induction of growth of surviving myocytes. The cardioprotective agents disclosed herein may also exert their effects on cells other than myocytes. These effects may lead to a reduction in size and/or partial or complete restoration of moderately injured and/or necrotic tissue of the affected area.

The drug eluting stent can be coated with single cardioprotective agent or combinations thereof, as well as with additional agents, such as, for example, anti-coagulating agents.

Provided herein are methods for treating an individual having (suffering from) an acute myocardial infarction and drug eluting stents useful for treating such individuals. These methods include treating an individual by introducing, such as by surgically inserting, at a site of an acute coronary artery occlusion upstream of the site of acute myocardial infarction, a drug eluting stent (DES) that comprises a cardioprotective agent that is released from the stent in a therapeutically effective amount. A therapeutically effective amount of a cardioprotective agent is an amount that, when administered to an individual as described herein, results in delivery of the cardioprotective agent to (presence of the cardioprotective agent in) the heart in an amount or concentration sufficient to assist or enhance repair of heart tissue and/or reduce (completely or partially) apoptosis of cardiomyocytes and, thus, reduce adverse effects on the heart.

Also provided herein are drug eluting stents that can be inserted at the site of an acute coronary artery occlusion upstream of the site of acute myocardial infarction. The drug eluting stent delivers a (at least one, one or more) cardioprotective agent, such as a tissue repair factor (e.g., cellular factors TGFβ1 and/or IGF1) to an individual after it is inserted into an individual. The drug eluting stent, in one embodiment, acts as an agent or drug delivery platform to enhance repair and/or reduce (partially or totally) apoptosis of myocytes, such as in the infarct border zone, and/or to maintain vessel patency after angioplasty.

Individuals who benefit from the method and stent described herein are humans who are suffering from or experiencing a cardiovascular event, such as acute myocardial infarction (AMI). Acute myocardial infarction is commonly known as a "heart attack."

The term "myocardial infarction" relates to changes in the heart muscle (myocardium) that occur due to the sudden deprivation of circulating blood, caused by events such as arteriosclerosis (narrowing or clogging of the coronary arteries) and thrombosis (clot), which reduce the flow of oxygen to the heart. The main change is death (necrosis) of myocardial tissue, which can lead to permanent damage or death of the heart muscle.

In one embodiment the invention provides methods for treating an individual having an acute myocardial infarction. These methods include treatment of an individual by surgically inserting an agent or drug eluting stent at a site of an acute coronary artery occlusion upstream of the site of acute myocardial infarction, for example during the PCI or coronary angiography procedures described herein.

In one embodiment, the eluting factor on the stent comprises a cardioprotective agent, which is released from the stent after it is introduced into an individual in need of treatment of myocardial infarction. In one embodiment the cardioprotective agent exerts its cardioprotective effects near or at the infarct border zone (a site of moderately injured, partially perfused, potentially salvageable tissue, comprising myocytes, at the periphery of developing myocardial infarcts).

In one embodiment the drug eluting stent is inserted at the time of the acute myocardial infarction, such as during the PCI or coronary angiography procedures described herein. The methods as described herein comprise inserting a drug eluting stent that comprises an eluting factor comprising a cardioprotective agent and may be carried out within 5 minutes, 10 minutes, 15 minutes, 30 minutes, 45 minutes, 1 hour, 2 hours, 3 hours, 6 hours, 12 hours, 18 hours, 24 hours, 30 hours, 36 hours, 48 hours, or 72 hours after the acute myocardial infarction.

In one embodiment methods described herein further comprise adjuvant therapy, or may be combined with any form of diagnosis (e.g. history, ECG, and cardiac markers) and/or treatment (prophylactic or stabilizing treatment, such as administering oxygen, aspirin, sublingual glyceryl trinitrate, and/or pain relievers, as well as treatment with beta blockers, anticoagulation agents, ACE inhibitors, and/or antiplatelet) prior to stenting and also treatment after stenting (e.g., treatment with anti-lipemic agents, anti-inflammatory agents, anti-thrombotic agents, fibrinolytic agents, anti-platelet agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), alpha-adrenergic blockers, beta-adrenergic blockers, cyclooxygenase-2 inhibitors, angiotensin system inhibitor, anti-arrhythmics, calcium channel blockers, diuretics, inotropic agents, vasodilators, vasopressors, thiazolidinediones, cannabinoid-1 receptor blockers and/or any combinations thereof).

Stents are commonly used during angioplasty and other revascularization procedures. One embodiment of a stent is a small, coiled wire-mesh tube that can be inserted into a blood vessel, such as an artery in the heart, that may be used to open a narrowed or clotted blood vessel. Stents may be permanently inserted into the artery during angioplasty. The stent may be expanded using a small balloon during the angioplasty procedure. When the balloon inside the stent is inflated, the stent expands and presses against the walls of the artery, which traps any fat and calcium buildup against the walls of the artery, allows blood to flow through the artery, and helps prevent the artery from closing again (restenosis). The stent may also help prevent small pieces of plaque from breaking off and causing a heart attack. Mesh-like stents allow blood vessel cells to grow through the mesh lining the stent and helping to secure it. The balloon is then deflated and removed, leaving the stent in place. Balloon angioplasty is often used to insert stents, although sometimes stents are placed without the use of a balloon, and other methods are known to those in the art.

Stents are provided that comprise a drug or agent that is released from the stent at a controlled rate and concentration over a specified time interval upon insertion, e.g. at a site of an acute coronary artery occlusion upstream of the site of acute myocardial infarction. These drug-eluting stents are stents that are coated with agents. These agents may be cardioprotective agents or other agents. Drug-eluting stents are known in the art and are described for example in U.S. Pat. Nos. 5,591,227, 5,697,967, 5,599,352, U.S. Publ. No. 2007/0077266, and PCT applications WO 01/12779, and WO 90/13332.

The invention provides, in one embodiment, drug eluting stents that deliver one or more cardioprotective agents, such as tissue repair factors (e.g., cellular factors TGFβ1 and IGF1). In one embodiment, the stent is coated with an eluting factor, from which the one or more cardioprotective agents is released after the stent is introduced into an individual. In other embodiments, the drug eluting stent releases cardioprotective agents and one or more additional agents (other than TGFβ1 and IGF1).

IGF1 eluting stents are known in the art for delivery of micromolar or nanomolar amounts of IGF1 into the coronary circulation, examples include: U.S. Pat. No. 6,660,034 covers the release of IGF1 and IGF2 from stents with sole objective of enhancing angiogenesis: U.S. patent Ser. No. 10/678,763 claims the release of Insulin like growth factors from stents with the objective of enhancing blood flow, it does not specify the IGF isoform or provide data on the dose, it is, focused on angiogenesis: U.S. Pat. No. 7,491,234 teaches the release of IGF1 over polymer coated vascular stent but does not indicate the therapeutic interest; U.S. Pat. No. 7,361,339 teaches the anti-apoptosis effects of IGF in acute MI but doesn't provide any data on the dose or the IGF1 release kinetics; U.S. Pat. No. 7,357,940 claims the release of IGF over polymer coated vascular stent but does not indicate the dose or the IGF release kinetics; U.S. Pat. No. 7,351,421 claims the release of IGF over polymer coated vascular stent, but does not indicate the dose or the IGF release kinetics: U.S. Pat. No. 7,332,160 claims the release of IGF over polymer coated vascular stent: U.S. Pat. No. 7,252,818 teaches IGF1 and IGF 2 for angiogenesis; U.S. Pat. No. 7,241,455 claims the release of IGF over polymer coated vascular stent; U.S. Pat. No. 7,101,857 claims the release of IGF over polymer coated vascular stent; U.S. Pat. No. 7,055,237 claims the release of IGF over polymer coated vascular stent; U.S. Pat. No. 7,022,132 claims the release of IGF over polymer coated vascular stent; U.S. Pat. No. 6,923,996 claims the release of IGF over polymer coated vascular stent; U.S. Pat. No. 6,830,577 claims the release of IGF over polymer coated vascular stent; U.S. Pat. No. 6,720,141 claims the release of IGF over polymer coated vascular stent but is focused at In-stent restenosis; U.S. Pat. No. 6,709,427 claims the release of IGF over polymer coated vascular stent; U.S. Pat. No. 6,613,084 claims the release of IGF over polymer coated vascular stent: U.S. Pat. No. 6,569,195 claims the release of IGF over to polymer coated vascular stent; U.S. Pat. No. 6,569,147 claims the release of IGF over polymer coated vascular stent; U.S. Pat. No. 6,258,121 claims the release of IGF over polymer coated vascular stent; U.S. Pat. No. 5,954,706 claims the release of IGF over polymer coated vascular stent; U.S. Pat. No. 6,379,382 teaches multiple drug coating on the stents and claims the release of IGF. The contents of all of these applications are incorporated herein by reference.

The cardioprotective agents and other agents, alone or in combination, can be combined with organic or inorganic carrier molecules, elution factors, solvents, salts, biopolymers, synthetic polymers and applied to the stent to generate a coated stent. Stent coating is known in the art and may involve immersion of the stent in a solution or may involve spray coating.

Drug-eluting stents may be coated with cells, such as endothelial cells engineered to express cellular factors that have, for example, cardioprotective, angiogenic, anti-thrombotic, antiplatelet, anticoagulant, antimicrobial, anti-inflammatory, antimetabolic, and/or vasoreactive effects, or may be directly coated with genes encoding polypeptides exerting similar effects. Drug-eluting stents may be coated with agents such as cardioprotective agents, angiogenic agents, anti-thrombotic agents, antiplatelet agents, anticoagulant agents, antimicrobial agents, anti-inflammatory agents, antimetabolic agents, and/or vasoreactive agents.

An anti-inflammatory factor or agent is, for example, a cytokine with inflammation inhibitory action, such as TGF-β, IL-4, IL-5, IL-10, IL-13, galectin-3. An angiogenic factor is for example a cytokine transmitting a signal for stimulation of angiogenesis, such as HGF, VEGF, bFGF, TNF-α or TP.

Agents that may be used for coating of drug-eluting stents may be derived from bioartificial polymeric materials obtained from blends of synthetic polymers with, for example, fibrin, thrombin and/or collagen, wherein for example a synthetic or biodegradable polymer is combined, for example through mixing, with fibrinogen and cross-linked with thrombin and then made into vascular grafts.

Suitable biostable and/or synthetic polymers include silicones, polyurethanes, polyesters, vinyl homopolymers and copolymers, acrylate homopolymers and copolymers, polyethers and cellulosics. Suitable bioabsorbable and/or biodegradable polymers include polyphosphate ester, polyhydroxybutyrate valerate, polyhydroxybutyrate-co-hydroxyvalerate, poly(L-lactic acid), poly(lactide-co-glycolide) and poly(hydroxybutyrate-co-valerate).

Drug-eluting stents can be generated by various methods known in the art. One such method comprises making or obtaining a solution which includes a solvent, a polymer dissolved in the solvent and a therapeutic agent, such as a cardioprotective agent, anti-thrombotic agent, antiplatelet agent, anticoagulant agent, antimicrobial agent, anti-inflammatory agent, antimetabolic agent, and/or vasoreactive agent as described herein, dispersed in the solvent to obtain a solution and applying the solution to the structural elements of a stent by immersing the stent into the solution or by spraying the solution onto the stent and evaporating the solution.

Any combinations of spreading, dipping or spraying using water and/or an organic solvent capable of dissolution of the agent and the binder component, such as a polymer followed by drying (natural drying or drying under reduced pressure or the like) may be suitable for generating a drug eluting stent, and such methods are known in the art. The inclusion of a polymer in intimate contact with a therapeutic agent or drug on the underlying stent structure allows the therapeutic agent or drug to be retained on the stent in a resilient matrix during expansion of the stent and also slows the administration of drug following implantation. The method can be applied whether the stent has a metallic or polymeric surface. The amount of drug to be included on the stent can be readily controlled by applying multiple thin coats of the solution while allowing it to dry between coats. The overall coating should be thin enough so that it will not significantly increase the profile of the stent for intravascular delivery by catheter, such as for example, less than about 0.002 inch thick or less than 0.001 inch thick. The adhesion of the coating and the rate at which the drug is delivered can be controlled by the selection of an appropriate bioabsorbable or biostable polymer and by the ratio of drug to polymer in the solution. By this method, therapeutic agents or drugs such as glucocorticoids (e.g. dexamethasone, betamethasone), heparin, hirudin, tocopherol, angiopeptin, aspirin, ACE inhibitors, growth factors, oligonucleotides, and, more generally, cardioprotective agents, antiplatelet agents, anticoagulant agents, antimitotic agents, antioxidants, antimetabolite agents, and anti-inflammatory agents can be applied to a stent, retained on a stent during expansion of the stent and elute the drug at a controlled rate. The release rate can be further controlled by varying the ratio of therapeutic agent or drug to polymer in the multiple layers.

For example, a higher drug-to-polymer ratio in the outer layers than in the inner layers would result in a higher early dose, which would decrease over time. A typical ratio of drug to dissolved polymer in the solution can vary widely (e.g. in the range of about 10:1 to 1:100). In one embodiment, the drug eluting stent provided comprises an eluting factor that comprises a (at least one, one or more) cardioprotective agent and is capable of releasing/releases the cardioprotective agent under physiological conditions/when the stent is present in the site of an acute coronary artery occlusion upstream of the site of acute myocardial infarction. In certain embodiments, the cardioprotective agent is released from the stent (from the eluting factor) within 5 minutes, 10 minutes, 15 minutes, 30 minutes, 45 minutes, 1 hour, 2 hours, 3 hours, 6 hours, 12 hours, 18 hours, 24 hours, 30 hours, 36 hours, 48 hours, or 72 hours after the stent is inserted into the individual. In another embodiment, the cardioprotective agent is released from the stent at a concentration of 0.01, 0.1, 1, 10, 100, or 1000 pg/ml or any concentration in between after the stent is inserted. The time after introduction of the stent into an individual at which release of the cardioprotective agent begins and the concentration or rate at which the cardioprotective agent is released can be varied as needed to provide a therapeutically effective amount of the cardioprotective agent in an appropriate time period (in sufficient time to have the desired effect of assisting or enhancing repair of heart tissue and/or reducing (completely or partially) apoptosis of cardiomyocytes and, thus, reducing adverse effects on the heart). The time of release after introduction of the stent into an individual and the concentration or rate at which the cardioprotective agent is released can be combined in any manner (e.g., release in a short time at a low concentration, fast release at a high concentration), in order to provide effective treatment. Further, a stent can comprise one or more cardioprotective agents (e.g., TGFβ1 alone or in combination with IGF1 and/or another cardioprotective agent: IGF1 alone or in combination with TGFβ1 and/or another cardioprotective agent). It can further comprise other agents (drugs), such as those that have anti-apoptotic effects and/or cardiotrophic effects, tissue repair factors, cytotoxic agent(s), cytostatic agent(s) or anti-coagulating agent(s).

As used herein, the term "cardioprotective agents" refers to agents that exert certain effects, such as anti-apoptotic and/or hypertrophic effects, that are beneficial to the patient or subject suffering from an acute myocardial infarction. Cardioprotective agents of the invention may exert their beneficial effects on cells such as for example myocytes in tissues such as heart tissues, but may also exert their effects on cells such as epithelial or endothelial cells present for example in arteries supplying the heart. When supplied sufficiently early after the occurrence of myocardial infarction the beneficial effects may include a reduction or prevention of cell death, such as through necrosis or apoptosis, of myocytes at the periphery of developing myocardial infarcts and/or an induction of growth of surviving myocytes. The cardioprotective agents may also stimulate growth or prevent cell death of epithelial or endothelial cells present in arteries supplying the heart. These effects may lead to a reduction in size and/or partial or complete restoration of the moderately injured and/or necrotic tissue of the infarcted area. Additional beneficial effects may include dissolving blood clots or other organic material leading to arterial constrictions or occlusions, such as vulnerable atherosclerotic plaques.

Cardioprotective agents disclosed herein that exert anti-apoptotic and/or hypertrophic effects include TGFβ1 and IGF1. Other cellular factors that are involved in tissue repair or maintenance, stem cell factors, anti-apoptotic factors and/or growth factors may also be useful as cardioprotective agents. Such agents include granulocyte colony stimulating factor (GCSF), platelet-derived growth factor (PDGF), vascular endothelial growth factor (VEGF), fibroblast growth factors (FGFs), Angiotensin II, and stromal cell-derived factor 1 (SDF-I).

TGF-β is a secreted protein that exists in three isoforms TGF-β1, TGF-β2 and TGF-β3. The TGF-β family is part of a superfamily of proteins known as the transforming growth factor beta superfamily, which includes inhibins, activin, anti-müllerian hormone, bone morphogenetic protein, decapentaplegic and Vg-I.

The insulin-like growth factors (IGFs) are polypeptides with high sequence similarity to insulin and comprise of cell-surface receptors (e.g. IGF1R and IGF2R), ligands (e.g. IGF-1 and IGF-2), IGF binding proteins (e.g. IGFBP 1-6), as well as associated IGFBP proteases. Insulin-like growth factor 1 (IGF-1) is mainly secreted by the liver as a result of stimulation by growth hormone (GH) and plays a role in the promotion of cell proliferation and the inhibition of cell death (apoptosis). Insulin-like growth factor 2 (IGF-2) is thought to be a primary growth factor required for early development while IGF-1 expression is required for achieving maximal growth.

Many cardioprotective agents disclosed herein, such as TGFβ1 and IGF1, are commercially available in purified or recombinant form and have been suggested for many therapeutic uses, such as for example wound healing (U.S. Pat. Nos. 4,861,757; 4,983,581 and 5,256,644), or induction of bone growth (U.S. Pat. Nos. 5,409,896 and 5,604,204).

The cardioprotective agents disclosed herein can also be combined with additional agents that have complementary, synergistic or additive effects. For example, drugs that lower cholesterol levels, such as statins, may enhance the responsiveness of cardiovascular cells to the protective actions of TGF-β, thus helping prevent the development of atherosclerosis and heart disease. In another examples, anti-coagulating agents such as Aspirin (salicylic acid), heparin, Coumadin, ethylenediamine tetraacetic acid (EDTA), citrate, ethylenebis(oxyethylenenitrilo) tetraacetic acid (EGTA), diethylenetriamine pentaacetic acid (DTPA), 1,2-diaminocyclohexane tetraacetic acid (DCTA) and others, may be combined with cardioprotective agents to help prevent arterial blockage. Vessel spasticity minimizing agents, such as haloalkylamine alpha adrenergic blocking agents, e.g. phenoxybenzamine, isomers of phenoxybenzamine and tertiary amines of phenoxybenzamine, and/or vasodilator agents, such as lidocaine, xylocaine, tetracaine, procaine and other short-term vasodilators such as papaverine, adenosine, nitric oxide donor agents, calcium channel blocker agents, sodium channel blocker agents and related adenosine regulating agents may also be combined with cardioprotective agents. Anti-inflammatory agents, such as non-steroidal anti-inflammatory drugs (NSAIDs), for example ibuprofen, aspirin and naproxen, or herbs with anti-inflammatory effects, such as hyssop, ginger, Turmeric, *Arnica montana* and willow bark may also be combined with cardioprotective agents.

Cardioprotective agents of the invention may also be combined with additional cardiovascular agents, such as aldosterone receptor antagonists, angiotensin converting enzyme inhibitors, angiotensin II inhibitors, centrally and peripherally acting antiadrenergic agents, antiadrenergic agents, antianginal agents, antiarrhythmic agents, beta-adrenergic blocking agents, cardioselective and non-selective beta blockers, calcium channel blocking agents, diuretics (e.g. loop, potassium-sparing, thiazide diuretics), carbonic anhydrase inhibitors, inotropic agents, vasodilators, renin inhibitors, sclerosing agents, and vasopressin antagonists.

Examples of alpha-adrenergic blockers include: doxazocin, prazocin, tamsulosin, and tarazosin.

Beta-adrenergic receptor blocking agents are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3~(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)~2-butanol, 2-(3-t-butylamino-2-hydroxy-propylthio)-4-(5-carbamoyl-2-thienyl)thiazol, 7-(2-hydroxy-3-t-butylaminpropoxy) phthalide. The above-identified compounds can be used as isomeric mixtures, or in their respective levorotating or dextrorotating form.

Patients without ST segment elevation are presumed to be experiencing either unstable angina (UA) or non-ST segment elevation myocardial infarction (NSTEMI). NSTEMI may be managed with medication (e.g. antiplatelet and anticoagulating agents) to prevent the narrowed artery from occluding, although PCI is often performed during hospital admission. In patients who have multiple blockages and who are relatively stable, bypass surgery of the blocked coronary artery may be an option. Coronary artery bypass surgery involves an artery or vein from the patient being implanted to bypass narrowing or occlusions on the coronary arteries. Several arteries and veins can be used, however internal mammary artery grafts have demonstrated significantly better long-term patency rates than great saphenous vein grafts.

Post-MI, several long-term medications can be used with the aim of preventing secondary cardiovascular events such as further myocardial infarctions, congestive heart failure or cerebrovascular accident (CVA). Antiplatelet drug therapy such as aspirin and/or clopidogrel, Beta blocker therapy such as metoprolol or carvedilol, ACE inhibitor therapy, Statin therapy, aldosterone antagonist agents, such as eplerenone, Omega-3 fatty acids, and/or stem cell treatment by coronary artery injections of stem cells derived from their the patient's own bone marrow, may be used.

Therapies for reducing the risk of a future cardiovascular event include but are not limited to diet and/or exercise and/or therapies with: anti-lipemic agents, anti-inflammatory agents, anti-thrombotic agents, fibrinolytic agents, anti-platelet agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), alpha-adrenergic blockers, beta-adrenergic blockers, cyclooxygenase-2 inhibitors, angiotensin system inhibitor, anti-arrhythmics, calcium channel blockers, diuretics, inotropic agents, vasodilators, vasopressors, thiazolidinediones, cannabinoid-1 receptor blockers and/or any combinations thereof.

This invention is not limited in its application to the details of construction and the arrangement of components set forth in the preceding following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Cardiotrophic effects of conditioned media (CM) derived from autologous circulating progenitor cells (CPCs) in a porcine myocardial infarction (MI) model were investigated and the cellular factors TGFβ1 and IGF1 were implicated to play a role in the observed beneficial effects. Landrace pigs (25-28 Kg) underwent MI generation via percutaneous transluminal balloon occlusion of the coronary artery for 80 minutes, followed by 120 minutes of reperfusion. Intracoronary conditioned media (CM) from autologous CPC or CM+anti-TGFβ1 or CM+anti-IGF1 or X-vivo 15 (control) was administered during balloon occlusion of the infarct related artery. At 24 hours or 8 weeks post MI, the animals were sacrificed, and the hearts underwent infarct quantification. Cardiomyocyte apoptosis within the MI borderzone (50% MI/50% normal myocardium/high power field) was evaluated by TUNEL staining, Caspase 9 and BCl-2 protein expression together with Caspase 3 and 9 activity assay. Functional analysis was performed using conductance pressure-volume catheters. CM therapy significantly reduced the infract size at 8 wks. In addition CM significantly reduced the apoptotic signal at 24 hours, and a significant improvement in cardiac function was observed at 24 hrs as well as 8 weeks post MI. The beneficial effects of CM were attenuated by blocking TGFβ1 and IGF1. Thus, CPC derived conditioned media reduces cardiomyocyte apoptosis in the MI borderzone 24 hours post MI generation, leading to an improvement in left ventricular function. These beneficial effects of CM are mediated substantially through TGFβ1 and IGF1.

Materials and Methods

Isolation and Characterization Circulating Progenitor Cells from Peripheral Blood:

Circulating progenitor cells (CPCs) were isolated from 30-40 mls of blood draw-n from an ear vein of female Landrace pigs under aseptic technique 48 hours before infarct generation, as previously described (Doyle BJ. et al., Stem Cells Dev. 2008 Jun. 18). Blood mononuclear cells were harvested from peripheral buffy coat preparations using Ficoll-Paque Plus (15 cc) separation. The cells were analysed for the expression of CPC markers (CD133, CD34, cKit, FLK1, VE-Cadherin and eNOS) by RT PCR and were compared to human CPCs. Total RNA was isolated from 24 hour cultured human and pig CPC using SV Total RNA Isolation kit (Progenia, Southampton, UK). 5 µg of total RNA was reverse transcribed using Superscript III First-Strand Synthesis Kit with poly-dT primers (Invitrogen, Carlsbad, Calif.). 2 µl of cDNA was used for each PCR reaction for stem/endothelial cell markers using Platium Taq Polymerase (Invitrogen, Carlsbad, Calif.) with the primers and annealing temperatures outline in Table 1 below. Amplicons were visualized on 1.5% agarose gel stained with SybrGreen I nucleic acid stain (Invitrogen, Carlsbad, Calif.).

TABLE 1

The following primer sequences and RT PCR conditions were used:

| Marker/Primer | | Sequence | Size of Product | Annealing Tm (° C.) | Sequence ID NO |
|---|---|---|---|---|---|
| CD133 | For | 5'-TCCTGGGGTTGCTGTTTATT-3' | 157 bp | 58 | 1 |
| | Rev | 5'-CATATCACCAAGAGGGAAACG-3' | | | 2 |
| cKit | For | 5'-GAGGAGATAAATGGAAAC-3' | 385 bp | 51 | 3 |
| | Hum-Rev | 5'-GAATCACGTTTTCTTCTC-3' | | | 4 |
| | Pig-Rev | 5'-GAATCACGTTTCCGTCTC-3'5' | | | 5 |
| CD34 | Hum-F | 5'-CCTGATGAATCGCCGCAGCTGGAGC-3' | 201 bp | 58 | 6 |
| | Hum-R | 5'-CCAGAAACGGCCATTCAGCAAGACA-3' | | | 7 |
| | Pig-F | 5'-GCTGATGAACCGTCGCAGTTGGAGC-3' | | | 8 |
| | Pig-R | 5'-CCAGAAACGGCCATTCAGCGAGGCA-3' | | | 9 |

TABLE 1-continued

The following primer sequences and RT PCR conditions were used:

| Marker/Primer | | Sequence | Size of Product | Anneling Tm (° C.) | Sequence ID NO |
|---|---|---|---|---|---|
| Flk-1 | For | TTATCGGAGAAGAACGTGGT | 412 bp | 55 | 10 |
| | Rev | TAATGCTCAGCAGGATGGCA | | | 11 |
| eNOS | For | 5'-GGTATGGATGAGTATGACGTG-3' | 171 bp | 51 | 12 |
| | Rev | 5'-TGTTCCGGCCGAGGG-3' | | | 13 |
| VE-Cadherin | For | 5'-AACTTCCCCTTCTTCACCC-3' | 368 bp | 51 | 14 |
| | Rev | 5'-AAGGCTGCTGGAAAATG-3' | | | 15 |
| G3PDH | For | 5'-CCATGTCGTCATGGGTGTGAACCA-3' | 251 bp | 59.9 | 16 |
| | Rev | 5'-GCCAGTAGAGGCAGGGATGATGTTC-3' | | | 17 |

Generation of Conditioned Media from Circulating Progenitor Cells:

To generate the conditioned media, the CPCs were washed three times in MCDB 131 supplemented with hydrocortisone, antibiotics, and 10 ng/ml VEGF. Following this step, cells were subsequently re-suspended in X-Vivo-15 medium (BioWhittaker) supplemented with VEGF (1 ng/ml), and seeded on fibronectin coated plates at a density of $4.9 \times 10^3$ cells per $mm^2$ in a modification of previously reported methodology (Assmus B. et al., Circulation. 2002; 106: 3009-17; Doyle BJ. et al., Stem Cells Dev. 2008 Jun. 18). After 48 hours of culture, conditioned cell-free media was harvested from the cell culture by centrifugation (600×g for 5 minutes) and filtration (0.2 μm) of the media. The condition media was screened for presence of cytokines using the RayBio Human Cytokine Antibody Array kit.

In-Vitro Screening for Anti-Apoptotic Effects of Conditioned Media Using Neonatal Cardiomyocytes:

Hearts were removed from 1 day old Fisher rats, and cardiomyocytes were isolated and cultured as previously described (Doyle BJ. et al., Stem Cells Dev. 2008 Jun. 18; Perez-Terzic C. et al., Circ Res. 1999; 84: 1292-301). In line with a pure cardiomyocyte preparation, these cells showed no evidence of neural or vascular cell contamination. Cardiomyocytes were incubated under hypoxic conditions (95% $CO_2$ 5% $O_2$) for 24 hours at 37° C., followed by normoxic condition for 24 hours at 37° C. to induce cell death by apoptosis. Before the induction of hypoxia the cardiomyocytes were treated with the following solutions: fresh media (X vivo-15 with 1 ng/ml VEGF), conditioned media (CM) obtained from porcine CPC cultures (as described above), conditioned media containing a 100-fold excess of neutralizing antibody to either TGFβ or IGF1 or $IgG_5$ and Purified porcine TGFβ (10-1000 pg/mL) or IGF1 (1-100 pg/mL). The apoptosis signal in the cardiomyocytes was quantified using commercial caspase 9 activity assay kit (Chemicon International, California, USA) and the data is expressed as percent of X-Vivo treated group.

Porcine Model of Myocardial Infarction:

39 female Landrace pigs weighing 25-30 kg were used in this study in accordance with the guidelines of Experimental Animal Ethics Committee of University College Cork. 20 out bred farm reared juvenile Landrace pigs underwent percutaneous balloon occlusion of the proximal left circumflex (LCx) coronary artery for 80 minutes. The chronic infarct group comprising 19 similar pigs had percutaneous proximal left anterior descending (LAD) coronary artery balloon occlusion for an identical balloon inflation period. This experimental protocol has been described in detail previously (Klein HH. et al., Basic Res Cardiol. 1984; 79: 440-7) Briefly all animals were pre-medicated with amiodarone 400 mg, aspirin 75 mg and clopidogrel 75 mg daily for 8-10 days prior to infarct generation. Following intramuscular injection of ketamine and xylazine, the animals received intravenous propofol to effect. Mechanical ventilation was carried out using a large animal Harvard Apparatus ventilator and supplemental oxygen (4-6 L/min) combined with isoflurane (1-4%) to maintain general anaesthesia. Under fluoroscopy a 3.0×13 mm (Boston Scientific, Galway, Ireland) angioplasty balloon was inserted in the proximal LCx (acute infarct group) or the proximal LAD (chronic group) using a 6¥ IMA guide catheter (Boston Scientific, Galway Ireland) introduced via a 7Fr arterial sheath from the right internal carotid artery. The balloon was inflated to 6-8 atm, ensuring complete angiographic occlusion of the target vessel with check angiography performed every 15-20 minutes during the infarct generation period. Significant ST-segment elevation was confirmed on electrocardiography in all cases. Malignant arrhythmias were defibrillated as necessary. The balloon was then deflated and removed to allow reperfusion for a total of 120 minutes. Check angiography confirmed TIMI-3 flow in the infarct related artery at initiation of reperfusion. An over-the-wire coronary balloon (3.0×12 mm. Boston Scientific Galway. Ireland) was then positioned at the site of prior vessel occlusion. Three cycles of 4 minute balloon inflation with intracoronary infusion of 4 ml of X-vivo/VEGF, conditioned media. CM+anti-IGF 1, CM+anti-TGFβ1, or CM+IgG was performed, with a period of 4 minutes of balloon deflation between each cycle. For the CM+anti-IGF1, CM+anti-TGFβ1, or CM+IgG group, the blocking antibody or the IgG was mixed in CM 15 mins prior to intracoronary delivery. Finally check angiography confirmed infarct related artery patency (TIMI-3 flow), and the animal was recovered.

24 hours (acute study) or 8 weeks (chronic study) after infarct generation, the animals underwent repeat coronary angiography to confirm infarct related artery TIMI-3 patency, via the left internal carotid artery as described above. Following completion of recording of haemodynamic parameters with the conductance catheter, the animals were sacrificed with an overdose of pentobarbitone. The hearts were explanted, weighed and sectioned in 5 mm transverse slices from apex to base (6-8 slices/heart). A representative mid ventricular slice ($3^{rd}$ or $4^{th}$ slice) was stained with 2% TTC. Images of the sections were captured using a 10 mega pixel digital camera. Infarct area was quantified with planimetry of the images using NIH Image J software (Maryland, USA). Myocardium was taken from infarct, borderzone and remote myocardial areas for OCT embedding and cryopreservation in liquid nitrogen.

Pressure-Volume Loop Protocol:

Pressure volume loops were recorded using a 5Fr pig tailed conductance catheter (Miller Instruments, Houstan Tex., USA) positioned in the left ventricular apex under fluoroscopic guidance prior to MI generation, during reperfusion, post treatment and immediately prior to sacrifice (24 hours-acute group, 8 weeks-chronic group). Recordings were taken in the steady state in sinus rhythm for a minimum of 10 minutes using a sample frequency of 250 Hz, using LabChart 5 Pro (AD Instruments Oxfordshire, UK) and off-line analysis off haemodynamic parameters was performed using PVAN ultra 1.0 software (AD Instruments Oxfordshire, UK). A minimum of 45 sec of pressure-volume recordings in the steady state was analysed per animal (n=3 per treatment group).

Histology

5 μM thick sections from OCT embedded infarct, border zone myocardium were cut for histological analysis. The sections were stained with haematoxylin and eosin, Sirius red or Mason's Trichrome. Representative slides from infarct borderzones of the chronic group (as defined above) were stained for collagen content with picrosirius red (Sirius red F3BA in aqueous picric acid). At least 36 high powered fields/treatment group were acquired using Nikon CCD camera attached to the Nikon microscope. Collagen content was quantified by expressing regions stained with picrosirius red as a percentage of the total infarct-borderzone area per high power field, employing an automated image analysis system (NIS Elements Basic Research software).

Apoptosis in Infarct Border Zone:

The apoptosis signals from the border zone myocardium were quantified using three different established methodologies namely TUNEL (immunofluorescence), protein expression of Caspase 9 and bcl-2 using Western blots and by measuring activity of caspase 3 and 9. The infarct borderzone was defined as a high power field composed of 50% normal myocardium and 50% infarct area. The total number of TUNEL positive cells was counted in 25 high power fields per animal, derived from 4 slides (Sum thickness) taken from 3 mid-ventricular slices using the In Situ Cell Death Detection Kit (Roche) according to the manufacturer's instructions. Nuclei were counter-stained with DAPI. The detection of the TUNEL positive signal within cardiomyocytes was validated by dual staining of the myocardium with anti-α sarcomeric actin (Sigma A2172) followed by Rhodamine conjugated goat anti-mouse IgM as secondary antibody (Chemicon AP 128R).

Protein Extraction and Western Blot:

Expression of caspase 9 and bcl-2 were evaluated by Western blot analysis. Tissue of infarct border zone were washed in ice-cold PBS, placed in lysis buffer (3 times the weight of sample in volume; 50 mm/L NaCl, 50 mmol/L NaF, 50 mmol/L sodium pyrophosphate, 5 mmol/L EDTA, 5 mmol/L EGTA, 2 mmol/L Na3VO4, 1% Triton X-100, 10 mmol/L HEPES; supplemented with Complete protease inhibitors [Roche]) and homogenised on ice. Samples were incubated 1 hour on ice, and then cleared of cellular debris by centrifugation (14,000 rpm; 10 min). Protein levels were assessed using Bradford reagent. One hundred micrograms of protein per sample was prepared in sample buffer and loaded on 12%, then transferred onto nitrocellulose membranes. Membranes were blocked in 5% milk and primary antibodies were applied caspase 9 (Stressgen), Bcl-2 (Abcam) over-night at 4° C. Membranes were washed and the appropriate secondary peroxidase-conjugated antibody (Jackson laboratories) was applied for 1 hour at room temperature. The bound antibodies were visualized by chemiluminescence (SuperSignal, Pierce). Bands corresponding to the correct molecular weight were quantified using Image J (NIH software).

Caspase 3 and 9 Activity Assay:

Protein extraction was performed as described above for Western blots but without the Complete protease inhibitors. The tissue lysate was used for the estimation of caspase 3 and 9 activity using the caspase 3 and 9 activity assay kit (Chemicon International, California. U.S.). Protein content of the lysate was determined using the Bradford Protein estimation method and the caspase 3 and 9 activities were expressed as Units/mg protein.

Cardiomyocyte Hypertrophy Assessment:

The mean cardiomyocyte size of pigs in each experimental chronic group was evaluated from frozen sections of the infarct borderzone, using established morphometric methodology (Doyle BJ. et al., Stem Cells Dev. 2008 Jun. 18; Senthil V. et al, Circ Res. 2005; 97: 285-92). Briefly, slides were incubated with anti-laminin antibody (Sigma L8271) and anti-α sarcomeric actin (Sigma A2172) and subsequently labelled with Alexa Fluor 488 (Molecular Probes) and goat anti-mouse IgM Rhodamine-conjugated antibody (Chemicon AP 128R). Cell nuclei were stained with DAPI. At least 3 distinct sections from the infarct borderzone in each animal, and a minimum 1000 cardiomyocytes were studied in each treatment group. Cell size was quantified by measuring cell surface area with laser confocal microscopy (Nikon TE 2000) and a 40× objective. Two-dimensional confocal images were acquired by scanning 1024×1024 pixels per image, and processed with NIS Elements Basic Research software.

Fabrication of IGF-1 Eluting Stent:

Programmable elution profile (PEP™) based on a biostable polymeric coating is employed in fabrication of the IGF1 eluting stent. Using the PEP™ technology, a bare metal stent surface is modified to optimise the surface properties before a polymer coating containing the IGF1 is applied. The polymer containing the entrapped drug(s) is then sprayed onto the primed stent. The PEP™ system uses two polymers such that 'programmed' release can be achieved using different PEP™ polymer combinations. The system has flexibility in that it can release water-soluble and water-insoluble drugs with fast or slow release rates. It has also been shown to deliver high and low molecular weight drugs.

A bare metal stent is de-greased (by treatment with NaOH under sonication followed with rinsing with distilled water and oven drying) and primed by contact with an alkoxysilane in an aprotic organic solvent (Toluene) in the presence of an acid catalyst (glacial acetic acid) resulting in the formation of covalent bonds. The treated stent is dried in high temperature (50-55° c.) under vacuum. The purpose of this priming step is to create a monolayer. A bridging polymer is then added on to this to enable attachment of biologically active agent such as IGF1. Carboxymethyl cellulose (CMC; molecular weight 5000-500,000), dextran or diisocyanate or combinations of these polymers are suitable for this purpose. The strength of the polymer is inversely proportional to the release of the biological agent. For a 24 hr IGF1 eluting stent IGF1 will be added to the polymer solution (0.025% CMC, 1 mole of a diamine and two moles of a diisocyanate group) to make final concentrations of 500-550 pg. This polymer/drug solution is sprayed into the stent surface from a piezoelectric nozzle with a 40 um orifice positioned by a micromanipulator. The solvent is evaporated in 30 minutes to leave a polymer/IGF 1 layer inside the stent. Processing variables, such as polymer molecular weight, viscosity, number of layers, layer thickness, drying time, temperature, humidity, and solvent type can influence kinetics and thus should be tightly controlled. The loading process is repeated seven times to develop IGF1 eluting stents with release kinetics over 7 days.

Example 1

Figure 1:
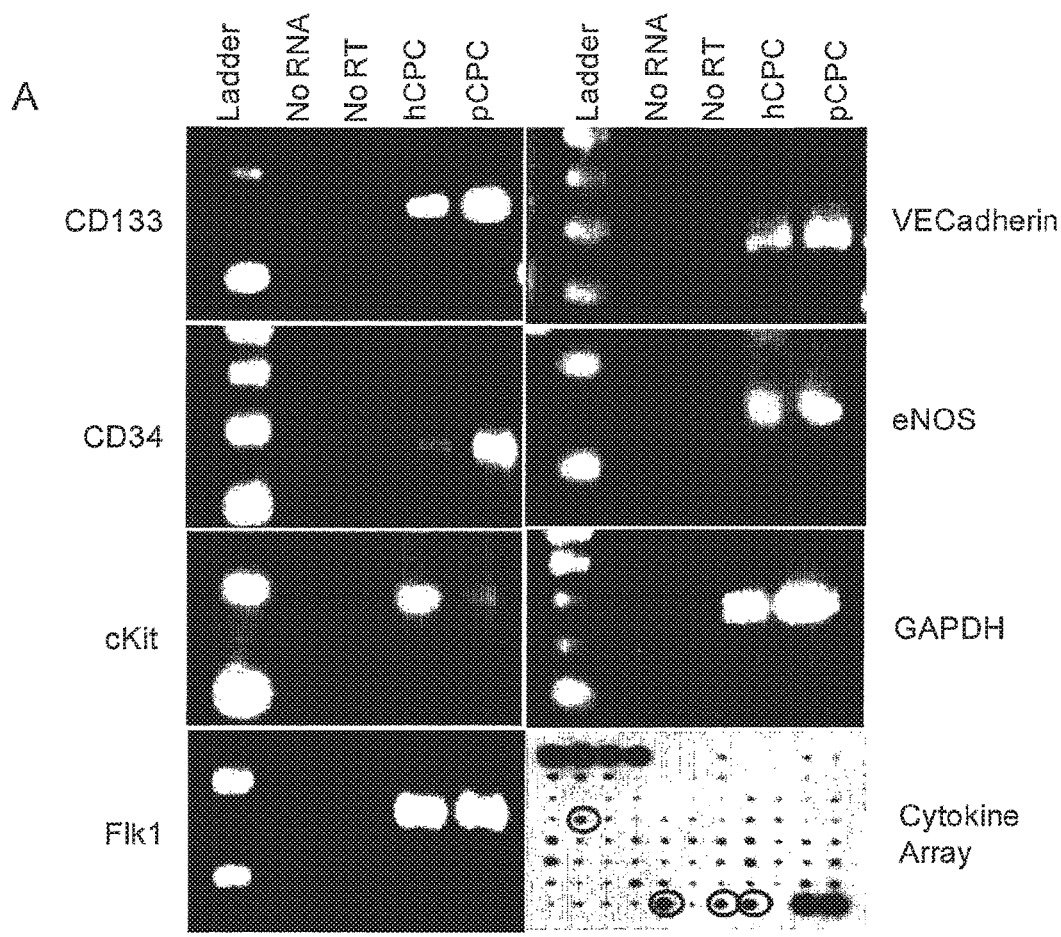
FIG. 1. Characterization of CPC, cytokine array of conditioned media (CM) and effect of CM on rat neonatal cardiomyocytes.
Figure 1:
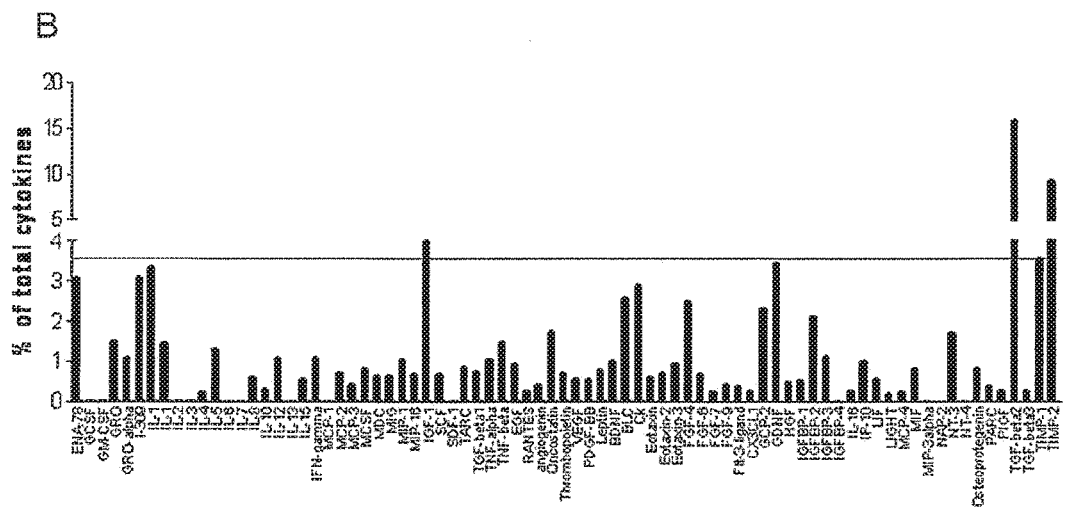
Figure 1:
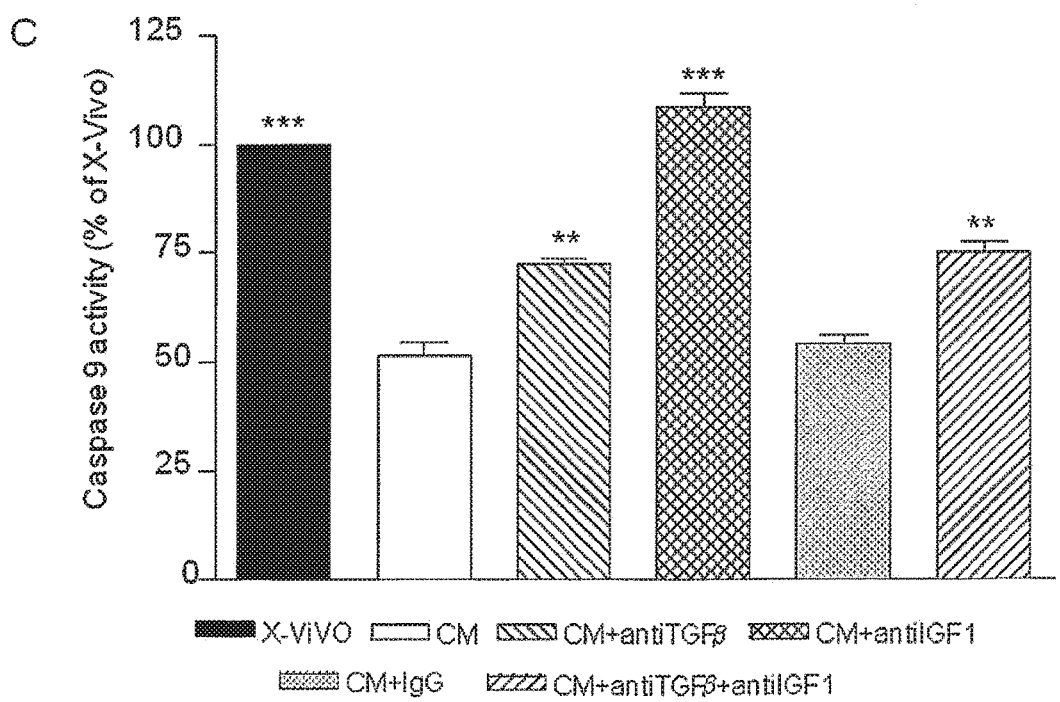
Figure 1:
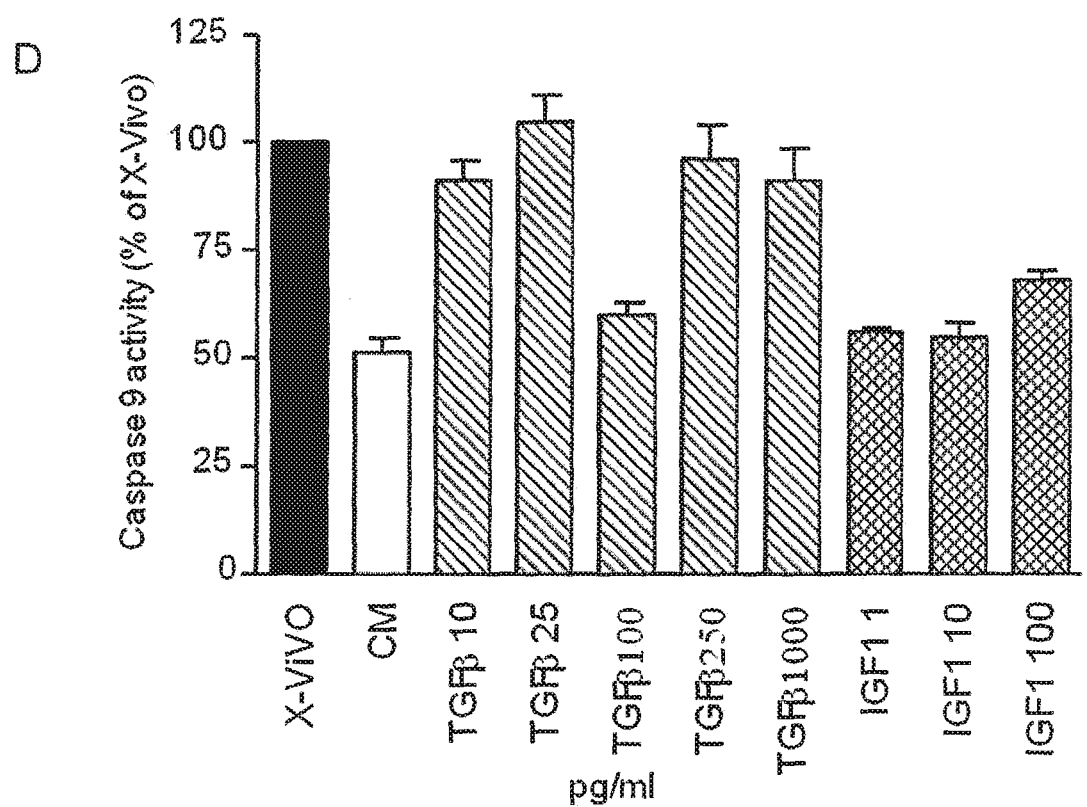

Characterization of Circulating Progenitor Cells and Cytokine Array of Condition Media Circulating progenitor cells (CPCs) isolated from peripheral blood mononuclear cells were characterized for expression of progenitor markers (CD133, CD34, cKit, Flk1, VECadherin, eNOS) using RT-PCR with GAPDH as a control (FIG. 1A).

The presence of cytokines was measured in cell-free conditioned media obtained from CPCs after 48 hours of culture and harvesting by centrifugation and filtration (0.2 μm). The conditioned media (CM) was screened for presence of cytokines using the RayBio Human Cytokine Antibody Array kit (FIG. 1A, bottom right panel).

The CM from CPC was screened for presence of about 78 different cytokines of which the TGFβ2 and IFG1 were the predominant growth factors (as measured in percent of total cytokines, see FIG. 1B).

Example 2

Antiapoptotic Effects of Condition Media in Neonatal Cardiomyocytes is Mediated by TGFβ and IGF1

Conditioned media significantly (about 50%) protected rat neonatal cardiomyocytes, isolated from hearts of 1 day old Fisher rats, from apoptosis induced cell death, when incubated under hypoxic conditions. Apoptosis was reduced by about 50% as judged by caspase 9 activity. Blocking TGFβ and IGF1 using specific neutralizing antibodies abrogated the protective effects of conditioned media (FIG. 1C). For neutralizing of TGFβ and IGF1, the CM was incubated with a 100-fold excess of anti-TGFβ and/or anti-IGF1 antibody for 15 minutes at 37° C. before exposing it to the cardiomyocytes. Purified TGFβ and IGF1 peptides mimicked the effects of CM at a narrow dose range (FIG. 1D). The data is expressed as Mean±SEM of % Caspase 9 activity to that of X-Vivo group in three independently performed experiments.

Example 3

Conditioned Media Protects the Borderzone Myocardium from Apoptosis at 24 Hours Post Myocardial Infarction The apoptosis signals from the border zone myocardium 24 hours post MI were quantified using TUNEL (immunofluorescence), protein expression of Caspase 9 and bcl-2 (Western blot) and by measuring activity of caspase 3 and 9 (Caspase activity assay kit).

The infarct borderzone was defined as a high power field (200×) composed of 50% normal myocardium and 50% infarct area. Conditioned media (CM) treated group had significantly ($p<0.001$) reduced TUNEL signals at the borderzone myocardium compared to the X-Vivo treated group (FIG. 2A, compare upper panel with lower panel).

The effects of CM were blocked by neutralizing TGFβ and IGF 1 in CM (FIG. 2B). The TUNEL signals from 5 sections/pig (N=3-4) with an average of 5 High power fields/section is expressed as Mean±SEM. A representative magnified (600×) image of border zone myocardium confirming the localization of TUNEL signal in the cardiomyocytes. Cardiomyocyte nuclei were counter-stained with DAPI and the cardiomyocyte character was validated by dual staining of the myocardium with anti-α sarcomeric actin (FIG. 2C).

The apoptotic signal in border zone myocardium 24 hrs post myocardial infraction was measured by Caspase 3 activity (FIG. 3A), Caspase 9 activity (FIG. 3B), and Caspase 9 protein expression (FIG. 3C). Caspase 3 and Caspase 9 activity, as well as Caspase 9 protein expression were significantly (p0.0001) reduced in the conditioned media (CM) treated group while the anti-apoptotic protein BCL2 (FIG. 3D) was significantly upregulated. The anti-apoptotic effects of CM are mediated by TGFβ ($p<0.001$) and IGF1 ($p<0.01$), since neutralizing antibodies to TGFβ and IGF1 significantly reduced the anti-apoptotic effects of CM. The data are expressed as Mean±SEM of border zone myocardium samples from 3-4 pigs/group.

The apoptotic signal in border zone myocardium 8 weeks post myocardial infraction was analyzed. Apoptotic markers, TUNEL positive nuclei (FIG. 4A), Caspase 9 activity (FIG. 4B). Caspase 3 activity (FIG. 4C) and BCL2 protein expression (FIG. 4D) were not effected at chronic time point (8 wks) post conditioned media therapy. The data are expressed as Mean±SEM of border zone myocardium samples from 3-4 pigs/group.

Example 4

Conditioned Media Reduces the Left Ventricular Infarct Area at 8 Weeks but not 24 Hrs Post Myocardial Infarction The effect of conditioned media on left ventricular infarct area was analyzed. 24 hours (acute study) or 8 weeks (chronic study) after infarct generation, the animals underwent repeat coronary angiography to confirm infarct related artery TIMI-3 patency, via the left internal carotid artery, sacrificed and the hearts explanted, weighed and sectioned in 5 mm transverse slices from apex to base (6-8 slices/heart). A representative mid ventricular slice ($3^{rd}$ or $4^{th}$ slice) was stained with 2% TTC.

Conditioned media (CM) therapy appears not to influence the left ventricular infarct area at 24 hrs post MI (FIG. 5A). However, CM therapy resulted in significant ($P<0.01$) reduction in the left ventricular infarct area at 8 weeks post MI (FIG. 5B). The data are expressed as Mean±SEM of 6-7 ventricular cross sections/pig heart with 3-4 pigs/group.

Example 5

Conditioned Media Therapy Improves Left Ventricular Function

The function of the left ventricular apex was analyzed 24 hrs and 8 weeks post MI. Conditioned media (CM) therapy significantly improved the left ventricular function i.e., ±dp/dt (FIG. 6A), ±dv/dt (FIG. 6B), stroke volume (FIG. 6C), and Ejection fraction (FIG. 6D) at 24 hrs post MI. The effects of CM appear to be mediated by TGF and IGF1. The data are expressed as Mean±SEM 20-25 cardiac cycles/pig with 3-4 pigs/group.

Conditioned media (CM) therapy significantly improved the left ventricular function i.e., ±dp/dt (FIG. 7A) ±dv/dt (FIG. 7B), stroke volume (FIG. 7C), and Ejection fraction (FIG. 7D) at 8 weeks post MI. The effects of CM at 8 weeks appear to be less dependent on TGF and IGF1. The data are expressed as Mean±SEM 20-25 cardiac cycles/pig with 3-4 pigs/group.

Example 6

Conditioned Media Effects on Border Zone Collagen Content

The effect of Conditioned media (CM) on border zone collagen content at 24 hrs and 8 weeks post MI were analyzed.

CM therapy significantly reduced the collagen content in the border zone myocardium at the acute (24 h, FIG. 8A) but not chronic (8 wks, FIG. 8B) time frame. The border zone sections were stained for collagen using picrosirus red and quantified using the NIH imageJ software. Collagen staining with picrosirus red on 5 sections/pig (n=3-4) with an average of 5 High power fields/section is expressed as Mean±SEM.

Example 7

Conditioned Media (CM) Increases Border Zone Cardiomyocyte Hypertrophy at 8 Weeks Post MI The effects of conditioned media (CM) on borderzone cardiomyocyte hypertrophy was analyzed. Cardiomyocytes were incubated with anti-laminin antibody and anti-α sarcomeric actin and subsequently labeled. Cell nuclei were stained with DAPI. At least 3 distinct sections from the infarct borderzone in each animal, and a minimum 1000 cardiomyocytes were studied in each treatment group.

CM significantly (p<0.001) increased border zone cardiomyocyte hypertrophy at 8 weeks post myocardial infarction (as measured by border zone cell surface area) and this effect was mediated by TGF and IGF1, as neutralizing antibodies to TGF and IGF1 decreased the hypertrphic effects mediated by CM (FIG. 9). An average of 300-400 border zone cardiomyocytes were analyzed per pig (with 3-4 pigs/group) and the data are reported as Mean±SEM of 1000-1600 cardiomyocytes/group.

Conditioned media therapy did not affect the total number of nuclei in the border zone myocardium at 24 h post MI (FIG. 10). Total number of DAPI positive nuclei/High power field were counted and expressed as Mean±SEM of 10 sections/animal.

Example 8

Antiapoptotic effect of conditioned media (CM) therapy on borderzone (BZ) myocardium in vivo (TUNEL staining) was abrogated by blocking IGF-1 in CM using selective neutralizing antibody. These data suggest that IGF-1 is the key cytoprotective factor in CM. The histogram data are expressed as mean±SEM (n=4). * P<0.01 versus CM treated group. FIG. 11.

Example 9

Effect of conditioned media on left ventricular infarct area at 8 weeks (A) post myocardial infarction (MI) was significantly reduced by CM therapy, which also increased thinning ratio (B) at 8 weeks post MI. Neutralizing antibody to IGF-1 in CM reversed these so beneficial effects. Data are expressed as mean±SEM of 7 ventricular cross sections/pig heart (each 5 mm thick) with 4 pigs/group. * P<0.01 versus CM treated group. FIG. 12.

Example 10

Antiapoptotic effect of IGF1 (50 and 500 pg/ml) therapy on borderzone (BZ) myocardium in vivo. Significant reduction in TUNEL staining was observed in the BZ myocardium of the IGF1 treated group. All histogram data are expressed as mean±SEM (n=4-5). * P<0.05 versus control group. FIG. 13.

Example 11

Evaluation of an IGF7 Eluting Stent for its Therapeutic Benefits (Myocardial Infarction Repair) in a Porcine Model of Myocardial Infarction The experimental protocols are approved by UCC animal ethics committee. Land race pigs (25-30 kgs) are put on aspirin (75 mg/day orally), plavix (75 mg/day orally) and amiodarone (300 mg/day orally) for a week before surgery. Anaesthesia is induced by a combination of Xylazine (2 mg/kg), ketamine (15 mg/kg) and glycopyrollate (0.01 mg/kg) and maintained by isofluorane (1.5-2%). The surgical site is cleaned with sterile gauze and smeared with betadine. A 5 cm incision is made 2 cm lateral and parallel to the trachea and by blunt dissection the carotid artery is exposed. Carotid arterial cut down is performed and interventional sheath placed to facilitate the insertion of balloon catheter and stent placement. The Philips fluoroscopy C arm is used to visualize the location and guiding the balloon and stent to its appropriate position in the coronary artery. Myocardial infarction is induced by percutaneous balloon occlusion of the left anterior descending coronary artery for 90 minutes followed by 2 hours reperfusion and will be sacrificed at 24 hours (acute) or 8 weeks (chronic) respectively. The IGF1 releasing stent is deployed at the site of balloon occlusion with the stent to artery ratio of 1.1:1. After the stent placement the catheters are pulled out and the arteriotomy site and the surgical wound is closed and smeared with betadine. 24 hr and 8 weeks post procedure the pigs are re-evaluated for myocardial function using pressure-volume loops and CT imaging and then euthanized by over does of pentobarbital. The heart and the coronary artery with stent are dissected out and processed for histological examination.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method of treating a mammal that has suffered a myocardial infarction to stimulate repair or survival of cardiac muscle damaged by the infarct, and to stimulate left ventricular remodeling, the method comprising a step of administering IGF-1 to the mammal by intracoronary infusion upstream of the myocardial infarction in sufficient quantity to reduce the effects of the myocardial infarction on the mammal by exerting anti-apoptotic and/or cardiotrophic effects on the affected or diseased tissue,
   wherein the IGF-1 is administered in a plurality of intracoronary infusions interspersed with periods during which the IGF-1 is not infused.

2. A method as claimed in claim 1, in which the intracoronary infusion is delivered through an angioplasty balloon.

3. A method as claimed in claim 1, in which the intracoronary infusion is delivered through an angioplasty balloon, and in which the balloon is inflated for the periods of infusion, and deflated during the non-infusion periods.

4. A method as claimed in claim 1, in which the IGF-1 is delivered at a concentration of from 1 to 100 pg/ml.

5. A method as claimed in claim 1, in which the IFG-1 is administered over a period of from 5 seconds to one hour.

6. A method as claimed in claim 1 in which the IFG-1 is administered over a period of from 1 to 30 minutes.

7. A method of treating a mammal that has suffered a myocardial infarction to stimulate repair or survival of cardiac muscle, and to stimulate left ventricular remodeling, the method comprising selecting an individual who has suffered a myocardial infarction and is in need of left ventricular remodeling, and administering IGF-1 to the mammal by intracoronary infusion upstream of the myocardial infarction in sufficient quantity to reduce the effects of the myocardial infarction on the mammal by exerting anti-apoptotic and/or cardiotrophic effects on the affected or diseased tissue,
   wherein the IGF-1 is administered in a plurality of intracoronary infusions interspersed with periods during which the IGF-1 is not infused.

\* \* \* \* \*